US006858395B2

(12) United States Patent
Kaufman

(10) Patent No.: US 6,858,395 B2
(45) Date of Patent: Feb. 22, 2005

(54) DIAGNOSTICS ASSAY METHODS AND AMELIORATION OF MUSCULAR DYSTROPHY SYMPTOMS

(75) Inventor: Stephen J. Kaufman, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 10/081,885

(22) Filed: Feb. 20, 2002

(65) Prior Publication Data

US 2002/0192710 A1 Dec. 19, 2002

Related U.S. Application Data

(60) Provisional application No. 60/286,890, filed on Apr. 27, 2001, and provisional application No. 60/270,645, filed on Feb. 20, 2001.

(51) Int. Cl.$^7$ ............................ G12N 33/53; G01N 1/30

(52) U.S. Cl. ...................................... 435/7.1; 435/40.52

(58) Field of Search ................................. 435/7.1, 40.52

(56) References Cited

U.S. PATENT DOCUMENTS

| | | | |
|---|---|---|---|
| 5,310,874 A | 5/1994 | Tamura et al. | |
| 5,561,047 A | 10/1996 | Shattil | |
| 5,780,244 A | 7/1998 | Engvall et al. | |
| 5,863,743 A | 1/1999 | Campbell et al. | |
| 5,985,846 A | 11/1999 | Kochanek et al. | |
| 6,057,423 A | 5/2000 | Brenner et al. | |

FOREIGN PATENT DOCUMENTS

| | | | |
|---|---|---|---|
| WO | WO 93/17031 | 9/1993 | |
| WO | WO 00/20582 | 4/2000 | |
| WO | WO 00/75187 | 12/2000 | ......... C07K/14/705 |

OTHER PUBLICATIONS

Acsadi, G. et al., "Dystrophin expression in muscles of mdx mice after adenovirus–mediated in vivo gene transfer." (Jan. 1996) *Human Gene Therapy* 7:129–140.
Amalfitano, A. and Chamberlain, J.S., "The mdx–amplification–resistant mutation system assay, a simple and rapid polymerase chain reaction–based detection of the mdx allele," (1996) *Muscle & Nerve* 19:1549–1553.
Belkin. A.M. et al., "β1D integrin displaces the β1A isoform in striated muscles: localization at junctional structures and signaling potential in nonmuscle cells," (1996) *J. Cell. Biol.* 132:211–216.
Belkin. A.M. et al., "Muscle β1D integrin reinforces the cytoskeleton–matrix link: modulation of integrin adhesive function by alternative splicing." (1997) *J. Cell Biol.* 139:1583–1595.
Bulfield. O. et al., "X chromosome–linked muscular dystrophy (mdx) in the mouse," (1984) *Proc. Natl. Acad. Sci. USA* 81:1189–1192.

Burkin. D.J. et al., "A functional role for specific spliced variants of the α7β1 integrin in acetylcholine receptor clustering," (1998) *J. Cell Biol.* 143:1067–1075.
Burkin. D.J. et al., "Laminin and α7β1 integrin regulate agrin–induced clustering of acetylcholine receptors," (2000) *J. Cell Sci.* 113:2877–2886.
Burkin, D.J. and Kaufman, S.J., "The α7β1 integrin in muscle development and disease," (Apr. 1999) *Cell Tissue Res.* 296:183–190.
Burkin. D.J. et al., "Enhanced expression of the α7β1 integrin reduces muscular dystrophy and restores viability in dystrophic mice," (Mar. 2001) *J. Cell Biol.* 152(6):1207–1218.
Campbell, K.P., "Three muscular dystrophies: loss of cytoskeleton–extracellular matrix linkage," (1995) *Cell* 80:675–679.
Campeau, P. et al., "Transfection of large plasmids in primary human myoblasts," (2001) *Gene Therapy* 8:1387–1394.
Cohn, R.D. et al., "Secondary reduction of α7B integrin laminin a2 deficient congenital muscular dystrophy supports an additional transmembrane link in skeletal muscle," (1999) *Journal of the Neurological Sciences* 163:140–152.
Cordier et al. (2000) "Rescue of skeletal muscles of γ–Sacroglycan–deficient mice with adeno–associated virus–mediated gene transfer," *Mol. Ther.* 1:119–129.
Deconinck, A.E. et al., "Postsynaptic abnormalities at the neuromuscular junctions of utrophin–deficient mice," (1997) *J. Cell Biol.* 136:883–894.
Deconinck, A.E. et al., "Utrophin–dystrophin deficient mice as a model for Duchenne muscular dystrophy," (1997) *Cell* 90:717–727.
Denetclaw, W.F. Jr. et al., "Myotubes from transgenic mdx mice expressing full–length dystrophin show normal calcium regulation," (1994) *Mol. Biol. Cell.* 5:1159–1167.

(List continued on next page.)

*Primary Examiner*—Phillip Gambel
*Assistant Examiner*—Maher Haddad
(74) *Attorney, Agent, or Firm*—Greenlee Winner and Sullivan PC

(57) ABSTRACT

The present disclosure provides compositions and sequences for the diagnosis, genetic therapy of certain muscular dystrophies, especially muscular dystrophy resulting from a deficiency in dystrophin protein or a combined deficiency in dystrophin and utrophin, and methods and compositions for the identification of compounds which increase expression of the α7 integrin. Expression of the integrin αBX2 polypeptide in muscle cells results in better physical condition in a patient or an animal lacking normal levels of dystrophin or dystrophin and utrophin. The present disclosure further provides immunological and nucleic acid based methods for the diagnosis of scapuloperoneal muscular dystrophy, where there is a reduction in or absence of α7A integrin expression in muscle tissue samples and normal levels of laminin-2/4 in those same samples. The present disclosure further provides methods for identifying compositions which increase the expression of α7 integrin protein in muscle cells of dystrophy patients.

3 Claims, 12 Drawing Sheets

OTHER PUBLICATIONS

DiMario. J.X. et al., "Fiber regeneration is not persistent in dystrophic (mdx) mouse skeletal muscle." (1991) *Dev. Biol.* 148:314–321.

Donoviel, D.B. et al., "Analysis of muscle creatine kinase gene regulatory elements in skeletal and cardiac muscles of transgenic mice," (1996) *Mol. Cell. Biol.* 16(4):1649–1658.

Ebihara, S. et al., "Differential effects of dystrophin and utrophin gene transfer in immunocompetent muscular dystrophy," (Sep. 2000) *Physiological Genomics* 3:133–144.

Engvall. E., "Muscle cell adhesion and muscular dystrophy," (Mar. 2000) *FASEB J* 14(4):A799[Abstract].

Fujii et al., "Targeted and stable gene delivery into muscle cells by a two–step transfer," (2000) *Biochem. Biophys Res. Commun.* 275:931–935.

George–Weinstein. M. et al., "In vitro and in vivo expression of $\alpha 7$ integrin and desmin define the primary and secondary myogenic lineages." (1993) *Developmental Biology* 156:209–229.

Gilbert. R. et al., "Efficient utrophin expression following adenovirus gene transfer in dystrophic muscle," (1998) *Biochem. & Biophys. Res. Communications* 242:244–247.

Grady, R.M. et al., "Subtle neuromuscular defects in utrophin–deficient mice," (1997) *J. Cell. Biol.* 136(4):871–882.

Grady, R.M. et al., "Skeletal and cardiac myopathies in mice lacking utrophin and dystrophin: a model for Duchenne muscular dystrophy," (1997) *Cell* 90:729–738.

Grady, R.M. et al., "Role for $\alpha$–dystrobrevin in the pathogenesis of dystrophin–dependent muscular dystrophies," (1999) *Nat. Cell Biol.* 1:215–220.

Gussoni, E. et al., "Dystrophin expression in the mdx mouse restored by stem cell transplantation," (Sep. 1999) *Nature* 401:390–394.

Hayashi, Y.K. et al., "Abnormal localization of laminin subunits in muscular dystrophies," (1993) *J. Neurol. Sci.* 119:53–64.

Hayashi, Y.K. et al., "Mutations in the integrin $\alpha 7$ gene cause congenital myopathy," (May 1998) *Nature Genetics* 19:94–97.

Hodges, B.I. and Kaufman, S.J., "Developmental regulation and functional significance of alternative splicing of NCAM and $\alpha 7\beta 1$ integrin in skeletal muscle," (1996) *Basic Appl. Myology* 6:437–446.

Hodges, B.L. et al., "Altered expression of the $\alpha 7\beta 1$ integrin in human and murine muscular dystrophies," (1997) *J. Cell Sci.* 110:2873–2881.

Jaynes, J.B. et al., "Transcriptional regulation of the muscle creatine kinase gene and related expression in transfected mouse myoblasts," (1986) *Mol. Cell Biol.* 6:2855–2864.

Johnson, J.E. et al., "Muscle creatine kinase sequence elements regulating skeletal and cardiac muscle expression in transgenic mice," (1989) *Mol. Cell Biol.* 9:3393–3399.

Kim, Y.Y. et al., "Cellular localization of $\alpha 3\beta 1$ integrin isoforms in association with myofibrillogenesis during cardiac myocyte development in culture," (1999) *Cell Adhesion and Comm.* 7(2):85–97.

Kwon, M.S. et al., "Calreticulin couples calcium release and calcium influx in integrin–mediated calcium signaling." (2000) *Mol. Cell Biol.* 11:1433–1443.

Law, D.J. et al., "Talin. vinculin and DRP (utrophin) concentrations are increased at the mdx myotendinous junctions following onset of necrosis," (1994) *J. Cell Sci.* 107:1477–1483.

Lee, H.C. et al., "Remission in models of type 1 diabetes by gene therapy using a single–chain insulin analogue," (2000) *Nature* 408:483–492.

Lim. L.F. and Campbell, K.P., "The sarcoglycan complex in limb–girdle muscular dystrophy," (1998) *Curr. Opin. Neurol.* 11:443–452.

Matsumura, K. et al., "Association of dystrophin–related protein with dystrophin–associated proteins in mdx mouse muscle," (1992) *Nature* 360:588–591.

Matsumura, K. and Campbell, K.P., "Dystrophin–glycoprotein complex: its role in the molecular pathogenesis of muscular dystrophies," (1994) *Muscle Nerve* 17:2–15.

Mayer, U. et al., "Absence of integrin $\alpha 7$ causes a novel form of muscular dystrophy," (Nov. 1997), *Nature Genetics* 17:318–323.

Miosge, N. et al., "Organization of the myotendinous junction is dependent on the presence of $\alpha 7\beta 1$ integrin," (Dec. 1999) *Laboratory Investigation* 79:(12):1591–1599.

Monaco, A.P. et al., "Isolation of candidate cDNAs for portions of the Duchenne muscular dystrophy gene," (1996) *Nature* 323:646–650.

Muzny, D.M. et al., GenBank Accession No. AC009799 (Mar. 2001) "Homo sapiens 12 BAC RP11–644F5".

Pons, F. et al., "Does utrophin expression in muscles of mdx mice during postnatal development functionally compensate for dystrophin deficiency," (1994) *J. Neurol. Sci.* 122:162–170.

Rafael, J.A. et al., "Skeletal muscle–specific expression of a utrophin transgene rescues utrophin–dystrophin deficient mice," (1998) *Nat. Gen.* 19:79–82.

Rafael. J.A. et al., "Dystrophin and utrophin influence fiber type composition and post–synaptic membrane structure," (2000) *Hum. Mol. Genet.* 9:1357–1367.

Ragot et al., "Efficient adenovirus–mediated transfer of a human minidystrophin gene to skeletal muscle of mdx mice." (1993) *Nature* 361:647.

Saher. G. and Hildt, F., "Activation of c–Raf–1 kinase signal transduction pathway in $\alpha$–integrin–deficient mice," (Sep. 1999) *J. Biol. Chem.* 274(39):27651–27657.

Shield, M.A. et al., "E–box sites and a proximal regulatory region of the muscle creatine kinase gene differentially regulate expression in diverse skeletal muscles and cardiac muscle of transgenic mice," (1996) *Mol. Cell Biol.* 16(9):5058–5068.

Sicinski, P. et al., "The molecular basis of muscular dystrophy in the mdx mouse: A point mutation," (1989) *Science* 244:1578–1580.

Song, W.K. et al., "Expression of $\alpha$ integrin cytoplasmic domains during skeletal muscle development: alternate forms, conformational change, and homologies with serine threonine kinases and tyrosine phosphatases," (1993) *J. Cell Sci.* 106:1139–1152.

Song, W.K. et al., "H36–$\alpha 7$ is a novel integrin alpha chain that is developmentally regulated during skeletal myogenesis," (May 1992) *J. Cell. Biol.* 117(3):643–657.

Stedman, H.H., "Molecular approaches to therapy for Duchenne and limb–girdle muscular dystrophy," (2001) *Current Opinion in Molecular Therapeutics* 3(4):350–356.

Tinsley, J.M. et al., "Amelioration of the dystrophin phenotype of mdx mice using a truncated utrophin transgene," (1996) *Nature* 384:349–353.

Turner, P.R. et al., "Increased protein degradation results from elevated free calcium levels found in muscle from mdx mice," (1988) *Nature* 335:735–738.

Vachon, P.H. et al., "Integrins (α7β1) in muscle function and survival," (Oct. 1997) *J. Clin. Invest.* 100(7):1870–1881.

von der Mark, H.J. et al., "Skeletal myoblasts utilize a novel β1–series integrins and not α6β1 for binding to the E8 and T8 fragments of laminin." (1991) *J. Biol. Chem.* 266:23593–23601.

Wang, B. et al., "Adeno–associated virus vector carring human minidystrophin genes effectively ameliorates muscular dystrophy in mdx mouse model," (Dec. 2000) *Proc. Natl. Acad. Sci. USA* 97(25):13714–13719.

Werner, A. et al., "Deletion of α7–integrin subunit leads to muscular dystrophy and late disappearance of postsynaptic folds in tonic muscle," (Oct. 1999) *Soc. Neuroscience* 25(1–2):2010 [Abstract].

Xiao et al., "Adeno–associated virus as a vector for liver–directed gene therapy," (1998) *J. Virol.* 72(12):10222–10226.-

1=α7BX2-mdx/utr (-/-)
2=mdx/utr (-/-)

1=α7BX2-mdx/utr (-/-)
2=mdx/utr (-/-)
3=mdx
4=wildtype mdx/utr (-/-) α7BX2-mdx/utr (-/-)

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:
      oligonucleotide useful as a primer

<400> SEQUENCE: 1
caagctgcac gcctgggtcc                                              20

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence:
      oligonucleotide useful as a primer

<400> SEQUENCE: 2
ggcacccatg acgtccagat tgaag                                        25

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence:
      oligonucleotide useful as a primer

<400> SEQUENCE: 3
catagttatt aatgcataga tattcag                                      27

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:
      oligonucleotide useful as a primer

<400> SEQUENCE: 4
gaacagcacc tttctggagg                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:
      oligonucleotide useful as a primer

<400> SEQUENCE: 5
ccttgaactg ctgtcggtct                                              20

<210> SEQ ID NO 6
<211> LENGTH: 1970
<212> TYPE: DNA
<213> ORGANISM: Homo sapiens

<400> SEQUENCE: 6
gaaagtagaa tcctggtgcc agccctgctg acagcatatg tatttcctta tagtacctgt  60
```

-continued

```
ttagagatgt gttagtgctc tggaggggat agccacaggt gtagtattgg aaaacagagg        120
gccagacttc caaatgtctg ttaacttatc caaggcaaag actgtcccag ggcagcagag        180
taagaaccca cttttttttt gttttcaaag aagtataatc ctgaacaatg aagtaggaaa        240
gacagaacac aggaagagga aggaggtagg acacttattg gaacttttaa gaaagggaaa        300
gagaagaaag aatcgtaaga atatgatagt gtttgaaggg cagagacaac actagaaaca        360
ttgagaaata ctctgagaaa gattccaagt gtggcagaga caagaatgat gacaaaatag        420
aatttgggat gagacaaaat cagatagtga gagagagaag ggaagatgga cagatgtata        480
ttcacaagac caacaccagt aagcaagggg agtaggaagg ggaagtggga gcattcgagg        540
ttcccattat gccaaattat ttcctgtctc tccttctggc cccatttctg tatcggagtt        600
ataaatagca gagagttgga aagtgtcccc ccacccccctt gcctctgtcc cagcctgagg       660
gaaagggaga ggaagaggga caggccaatg ggtccctgtg gagatcccat ctcagcccca        720
cccaggtcct gctgagccag tccaggactc tgcccctcc catccccttt catggatagg         780
aaatgtgcag tcctgggacg ggtctggtag ctggggacac cctttacatc cctctgcctc        840
ttgggtccag tctctttcat ctttgccttc tttgacaccc actcccctcc ccactgctta        900
atttcctctt cctgtaatca tccccagtcg ttttctttc tcccttcatt ccatcccttg        960
tcaattaatc tcttgcccctt cttctttcct ctctattcct ttccttttc catttctcca      1020
tttgctcccc gtatctcccg agtttctctc tctcttcttg cctctttttc tctgttccct       1080
tgaatcctga cgatgtggct agcactgctg tggtcattgc cgggctgggg gcggggatg        1140
ggataggatg ggggagggca gcggtctgat cccaacagca gaaagagtgc tctatgtgac       1200
catgggggaa cagggagcac taagatgcca cgctgcaccc aggcccagga cggctcccct      1260
ttcatttcct ctctatctgc acatctctct tcccaggttg tcttttagcg tcttcccaac      1320
ttctcatctc ttaccctcct tcctctgttt cagcccctct cttctatct gtacttctct        1380
ccctccgcat tccaaggcgc cgcctccacc actcccgggg tggggatggg gttggggag       1440
aaggggagga gagcgccgcg caggggcgga gccggagacg gtgctgggct tgggggcgt        1500
ggtggtgggg ggtcagcaag gctagtttcc atcccagcca ccagcctggg catccccttg     1560
gagacgggct tgggtctcca cctgccgcgg gagcgagggg cggggccgga ggcggggcct     1620
gagtggcgtc cccgggagag gaggcgggag ccggagtggg cgccggagct gcggctgctg     1680
tagttgtcct agccggtgct ggggcggcgg ggtggcggag cggcggccgg gcgggagggc     1740
tggcggggcg aacgtctggg agacgtctga aagaccaacg agactttgga gaccagagac     1800
gcgcctgggg ggacctgggg cttggggcgt gcgagatttc ccttgcattc gctgggagct    1860
cgcgcaggga tcgtcccatg gccggggctc ggagccgcga cccttggggg gcctccggga     1920
tttgctacct ttttggctcc ctgctcgtcg aactgctctt ctcacgggct                 1970
```

DIAGNOSTICS ASSAY METHODS AND AMELIORATION OF MUSCULAR DYSTROPHY SYMPTOMS

CROSS REFERENCE TO RELATED APPLICATIONS

This application claims priority from United States Provisional Application 60/270,645 filed Feb. 20, 2001 and from United States Provisional Application 60/286,890 filed Apr. 27, 2001, both of which are incorporated herein.

ACKNOWLEDGMENT OF FEDERAL RESEARCH SUPPORT

This invention was made, at least in part, with funding from the National Institutes of Health. Accordingly, the United States government has certain rights in this invention.

BACKGROUND OF THE INVENTION

The field of the present invention is the area of medical treatment and diagnosis using molecular technology. In particular, the present invention utilizes gene therapy and drug induced gene expression to ameliorate the physical condition of muscular dystrophy patients, especially those lacking dystrophin or lacking dystrophin and utrophin or those with lower than normal levels of $\alpha 7$ integrin, and in another aspect, this invention relates to the use of nucleic acid probes or primers or immunological probes for detecting the reduction of or lack of expression of the $\alpha 7\beta 1$ integrin in scapuloperoneal muscular dystrophy (SPMD) as well as to the use of assays to identify compounds which induce increased expression via $\alpha 7\beta 1$ integrin transcriptional regulatory sequences.

Scapuloperoneal (SP) muscular dystrophy, is one of a heterogeneous group of scapuloperoneal syndrome affecting the muscles of the shoulder girdle and peroneal. SP syndromes were formerly grouped as one genetic disease, but clinical analysis and genetic mapping have revealed that this syndrome includes at least two distinct diseases with different underlying genetic defects. SPMD is an autosomal dominant disorder characterized by myopathy and progressive muscle weakening in the shoulder girdle and peroneal muscles. The disease has late onset, with affected individuals first displaying symptoms in their late teens or early twenties and up to the late fifties. This disease affects the legs and feet (with foot drop and hammer toes) and the proximal and/or distal arms. Patients have scapular winging and asymmetry. There is intolerance to exercise. Other symptoms include contractures, hearing loss twitching muscle cramps, facial weakness and cardiac disorders. Death results from cardiac or respiration failure. Although the underlying genetic defect has not been identified previously, SPMD has been mapped by genetic linkage analysis to human chromosome 12q13.3-q15.

The defective association of skeletal and cardiac muscle with their surrounding basal lamina underlies the pathologies associated with a variety of muscular dystrophies and cardiomyopathies (Matsumura and Campbell, 1994, Hayashi, et al., 1993; Hayashi, et al., 1988; Lim and Campbell 1998). Duchenne Muscular Dystrophy (DMD) is a congenital X-linked myopathy that is caused by a lack of the dystrophin protein and affects approximately 1 in 3300 males. Patients with DMD experience progressive muscle deterioration and debilitation that severely restricts mobility. Death due to cardiac and respiratory failure usually occurs in the second decade of life.

Mutations in the dystrophin gene result in a lack of dystrophin, a 427 kDa protein localized to the inner cytoplasmic side of the plasma membrane of skeletal and cardiac muscle cells (Monaco et al., 1986; Matsumura and Campbell, 1994; Campbell, 1995). In association with dystroglycans, syntrophins, and sarcoglycans, dystrophin links the cell cytoskeleton to laminin in the extracellular matrix. In the absence of one or more components of the dystrophin linkage system, the association of fibers with the surrounding basal lamina is compromised, leading to the myopathy observed. Thus, the molecular continuity between the extracellular matrix and the cell cytoskeleton is essential for the structural and functional integrity of muscle.

The integrins are $\alpha\beta$ heterodimeric receptors that bind extracellular matrix proteins and interact with the cell cytoskeleton (Hynes, 1992). The $\alpha 7\beta 1$ integrin is a laminin receptor on skeletal and cardiac muscle (Song et al., 1992) and serve as a transmembrane link between the basal larnina and muscle fibers. Multiple insoforms of the $\alpha 7$ and $\beta 1$ chains are generated by developmentally regulated RNA splicing resulting in a family of receptors with diverse structure and functions (for reviews see Hodges and Kaufman, 1996 and Burkin and Kaufman, 1999).

The $\alpha 7$ integrin chain is encoded by a single autosomal gene on human chromosome 12q13 (Wang et al., 1995). Three alternative cytoplasmic domain ($\alpha$, 7A, B and C) and two extracellular domain variants (X1 and X2) of the protein have been identified (Song, et al., 1993; Collo et al., 1993, Ziober et al., 1993). Four additional alternatively spliced isoforms of the extracellular domain have been predicted by nucleotide sequence analysis (Leung et al., 1998; Vigner, et al., 1999).

The $\alpha 7\beta 1$ integrin is a major laminin receptor that serves as a transmembrane link and signal transduction mechanism between the extracellular matrix and the muscle fiber (Song et al., 1992, Hodges and Kaufman, 1996; Burkin and Kaufman, 1999). Alternative cytoplasmic domains (A, B and C) Song et al. 1993; Collo et al., 1993; Zoiber et al. 1993) and extracellular domains (X1 and X2) (Zoiber et al., 1993, Hodges and Kaufman, 1996) of this integrin are generated by developmentally regulated alternative RNA splicing. The diversity in the $\alpha 7$ integrin chain appears to be the result of the broad range of biological functions with which it is associated during muscle development, including the development of neuromuscular junctions (Burkin et al., 1998; Burkin et al., 2000), stability of myotendinous junctions and overall muscle integrity (Hayashi et al., 1998).

The $\beta 1$ chain cytoplasmic domain also undergoes developmentally regulated alternative splicing $\beta 1A$ is the most common isoform of the $\beta 1$ chain and is expressed in a wide variety of tissues including replicating myoblasts. The alternative $\beta 1D$ form is generated upon differentiation of myoblasts to myofibers (Zhidkova et al., 1995; van der Flier et al., 1995, Belkin et al., 1996; Belkin et al., 1997).

Mutations in the genes that encode the many components of the dystrophin glycoprotein complex cause the majority of muscular dystrophies. Mutations in the $\alpha 7$ gene also cause congenital myopathics (Hayashi et al., 1998). Thus, both the integrin and dystrophin-mediated transmembrane linkage systems contribute to the functional integrity of skeletal muscle. Interestingly, there is an increase in the amount of $\alpha 7$ transcript and protein in DMD patients and mdx mice (the mouse model that has a mutation in its dystrophin gene) (Hodges et al., 1997). This led us to suggest that enhanced expression of the integrin may partially compensate for the absence of the dystrophin glycoprotein complex (Hodges, et al., 1997; Burkin and Kaufman, 1999). Utrophin, a protein homologous to dystrophin, is also increased in DMD patients and mdx mice (Law, et al., 1994). Utrophin associates with many of the same proteins as dystrophin, and further increasing utrophin may, in part, also compensate for the absence of dystrophin (Tinsley et al., 1996).

Although DMD patients (Monaco et al., 1987) and mdx mice (Bulfield et al., 1984; Sicinski, 1989) both lack distrophin, the pathology that develops in the mdx mouse is much less severe than that observed in humans. The differences in the extent of pathology may be due to a number of factors including the enhanced expression and altered localization of utrophin (Law; et al., 1994; Pons et al., 1994) and the α7 integrin chain (Hodges et al., 1997) in mdx mice. In addition, differences in utilization of skeletal muscles by humans compared to mice in captivity may also contribute to the decreased level of pathology seen in mdx mice. In contrast, mdx/utr (−/−) mice lack both of dystrophin and utrophin and have a phenotype that is similar to that seen in Duchenne patients. These double mutant mice develop severe progressive muscular dystrophy and die prematurely between 4–20 weeks of age (Grady et al. 1997b, Deconinck, et al., 1997b).

To explore the hypothesis that enhanced expression of the α7β1 integrin compensates for the absence of the dystrophin glycoprotein complex and reduces the development of severe muscle disease, transgenic mice were made that express that rat α7 chain. The mdx/utr (−/−) mice with enhanced expression of the α7BX2 chain isoform show greatly improved longevity and mobility compared to non-transgenic mdx/utr (−/−) mice. Transgenic mice maintained weight and had reduced spinal curvature (kyphosis) and joint contractures. Transgenic expression of the α7BX2 chain also reduced the degree of mononuclear cell infiltration and expression of fetal myosin heavy chain (fMyHC) in muscle fibers. Together these results show that enhanced expression of α7BX2β1D integrin significantly reduces the development of muscular dystrophy.

Muscle fibers attach to laminin in the basal lamina using the dystrophin glycoprotein complex and the α7β1 integrin. Defects in these linkage systems result in Duchenne muscular dystrophy, β2 laminin congenital muscular dystrophy, sarcoglycan related muscular dystrophy, and α7 integrin congenital muscular dystrophy. Therefore the molecular continuity between the extracellular matrix and cell cytoskeleton is essential for the structural and functional integrity of skeletal muscle. To test whether the α7β1 integrin can compensate for the absence of dystrophin, we have expressed the rat α7 chain in mdx/utr (−/−) mice that lack both dystrophin and utrophin. These mice develop a severe muscular dystrophy highly akin to that observed in Duchenne muscular dystrophy, and they also die prematurely. Using the muscle creatine kinase promoter, expression of the α7BX2 integrin chain was increased approximately 2 3-fold in mdx/utr (−/−) mice. Concomitant with the increase in the α7 chain, its heterodimeric partner, β1D, was also increased in the transgenic animals. The transgene expression of the α7BX2 chain in the mdx/utr (−/−) mice extended their longevity by three-fold, reduced kyphosis and the development of muscle disease, and maintained mobility and the structure of the neuronmuscular junction. Thus bolstering α7β1 integrin mediated association of muscle cells with the extracellular matrix alleviates many of the symptoms of disease observed in mdx/utr (−/−) mice and compensates for the absence of the dystrophin- and utrophin- mediated linkage systems.

There is a longfelt need in the art for definitive and accurate methods for the diagnosis of particular types of neuromuscular disorders, such as SPMD, and to characterize the particular defects of the disorder. Direct or indirect (e.g. drug) treatment is likewise unavailable, through need. Enhanced expression of the α7β1 integrin provides a novel approach for and fulfills a longfelt need for treatment of Duchenne muscular dystrophy and other muscle diseases that arise due to defects in the dystrophin glycoprotein complex.

SUMMARY OF THE INVENTION

The present invention provides compositions and methods for ameliorating the physical condition and mobility of muscular dystrophy patients, for example, those suffering from Duchenne muscular dystrophy. There is also the beneficial result of longer life and better quality of life for patients treated according to the teachings and methods of the present invention. The present disclosure shows that expression over normal levels of the integrin polypeptide α7BX2 in muscle cells results in improved physical condition and mobility in the mouse model for Duchenne muscular dystrophy. Such overexpression also benefits individuals suffering from or susceptible to other forms of muscular dystrophy in which there is a deficiency in dystrophin and/or utrophin or α7 integrin. Similar improvements are achieved with the overexpression of the α7BX2 integrin polypeptide in human muscular dystrophy patients as well, either due to expression of an α7BX2 transgene specifically in muscle cells of human MD patients or due to increased expression of the naturally occurring gene due to stimulation of expression by the administration of a therapeutic composition with that effect. Human patients are similarly improved with respect to physical parameters and quality and length of life by the administration of compositions which improve the stability of the integrin protein. The expression of the α7BX2 coding sequence under the control of a muscle specific promoter in a human patients results in increased levels of the β1D polypeptide as well, with the result of increased function and quality of life. Any suitable vector for introducing the specifically regulated α7BX2 coding sequence can be used in the treatment of muscular dystrophy patients, with administration according to art-known methods. Intravenous or intramuscular administration or regional perfusion of a viral or plasmid vector comprising the muscle cell-specific expression construct is a desirable route of administration. Retroviral vectors, adenovirus and adeno-associated vectors are known and available to the art. Alternatively, the patient's myoblasts or stem cells can be harvested, transfected with a vector containing the muscle cell-specific expression construct, selected and expanded or ex vivo and then reintroduced into the patient by the intravenous route. Patients suffering from other forms of muscular dystrophy where α7 integrin protein levels are below normal similarly benefit from expression of an exogeneous α7 coding sequence so that increased amounts of α7β1 protein are increased in muscle cells, with the results that the symptoms of muscular dystrophy are ameliorated.

As an alternative to the use of gene therapy to increase α7BX2 expression in the muscular dystrophy patient, one can administer a composition effective for enhancing the level of expression of the patient's own α7BX2. The present invention provides methods for screening for enhanced α7BX2 expression: one of ordinary skill in the art can use quantitative (semi-quantitative) reverse transcriptase polymerase chain reaction (RT-PCR) assays or Northern hybridizations which allow determination of relative amounts of mRNA. Alternatively, one can monitor expression of state-of-the-art reporter molecules (e.g. green fluorescent protein, luciferase, β-galactosidase, β-lactamase, β-glucosidase), to evaluate drug-induced expression of the α7 integrin promoter linked to sequences encoding the reporter. Muscle cells or myogenic cells in culture are treated with test compositions and the amounts of α7BX2 or α7-specific transcripts are determined in response to a test compositions in comparison to a control which has not treated with the test composition. Expression is enhanced in response to the test composition when the level of α7BX2 or α7-specific transcript is greater in the presence than in the absence of the test composition. Alternatively, the amount of relative amount of α7BX2 or α7 protein is determined after growth of the muscle or myogenic cells in the presence and absence of the test composition. The amount or relative amount can be determined using α7BX2 or α7-specific antibody using any of known immunological assays: radioactive immunoassay, western blotting, enzyme-linked immunoassays, sandwich immunoassays and the like. As an alternative to an immunological methods, the amount or relative amount of the protein can be determined by the use of muscle or myogenic cells transformed with a fusion protein coding sequence for an α7BX2 protein linked to a green fluorescent protein sequence, or enzymatic reporters such as luciferase, β-lactamase, β-galactosidase, or β-glucuronidase, among others, or an immunological tag portion which can then allow specific immunlogical measurement of the target fusion protein. Such a fusion protein is expressed under the regulatory control of the native α7 promoter. Compositions identified by any of the assay methods noted above are used in the amelioration of muscular dystrophy symptoms by stimulating or increasing expression of the patient's own gene. The α7BX2-mdx/utr (−/−) mice can also be used for in vivo assays for compounds which ameliorate muscular dystrophy, by treating the mice with test compounds and observing an improvement in physical status.

Also within the scope of the present invention are methods for the diagnosis of muscular dystrophies which are characterized by lower than normal levels of α7 integrin protein, especially scapuloperoneal muscular dystrophy (SPMD). SPMD is diagnosed when the transcriptional or transitional expression of the α7A integrin isoform is reduced in muscle tissue biopsy samples taken from a patient exhibiting muscular dystrophy symptoms. Detection of α7A integrin expression can be via immunological analysis, or it can be via α7A integrin specific hybridization probes or using α7A integrin-specific primers for use in a reverse transcriptase polymerase chain reaction assay with the detection of the α7A integrin amplification product of a specific size, as described herein below. Using the particular primers described hereinbelow, the α7A amplification product is 451 bp whereas the amplication product produced from α7B transcript is 338 bp in length. The percent reduction in α7A expression parallels the severity of disease. SPMD is further characterized in that patients with this disorder exhibit normal levels of 2/4 laminin expression.

In a method for diagnosing SPMD in an individual, first a sample of muscle tissue from the individual is provided and, if necessary, treating to render the components of the tissue available for antibody binding, the muscle tissue sample being characterized by levels of the a7A integrin protein; contacting the muscle tissue sample with an antibody which specifically binds to the α7A integrin protein, wherein said contacting under conditions appropriate for binding of the antibody to the α7A integrin protein; detecting the extent of binding of the antibody to the α7A integrin protein in the muscle tissue sample; and comparing the extent of binding of the antibody specific for the α7A integrin protein in the muscle tissue sample from the individual for whom diagnosis is sought to the extent of binding of the antibody specific for the α7A integrin protein in a muscle tissue sample from a normal individual, wherein a substantial reduction in the extent of binding of the antibody specific for the α7A integrin protein in the muscle tissue sample from the individual for whom diagnosis is sought as compared with the extent of binding in the muscle tissue sample of a normal individual is indicative of SPMD (scapuloperoneal muscular dystrophy). Desirably the muscle tissue samples are from skeletal muscle tissue. Histological specimens from an individual for whom diagnosis is sought and from a normal individual can also be used with antibody detection methods. Detection of the bound antibody can be via a detectable label such as a fluorescent compound, a chemiluminescent compound, radioactive label, enzyme label or other label known to the art, coupled with detection methods obvious in choice to one of ordinary skill in the art. A second antibody which recognizes the (first) integrin-specific antibody can be labeled and used to detect the bound first antibody. Advantageously, assays can be run in parallel for the assessment of the expression of 2/4 laminin in the individual for whom diagnosis is sought (and in a normal (control) sample. In an SPMD patient, the laminin levels are within the normal range.

The diagnostic method of the present invention can also be based on western blot analysis. In such a method the muscle tissue samples are solubilized, the components are separated by electrophoresis, for example, polyacrylamide gel electrophoresis or sodium dodecyl sulfate polyacrylamide gel electrophoresis, the separated components are transferred to a solid support to form an immunoblot, the immunoblot is contacted with antibody specific for the α7A integrin protein under conditions appropriate for the binding of the antibody to the cognate integrin protein, the non-specifically bound material is removed, and the specific binding of the antibody to the α7A integrin protein is detected, and the extent of the antibody binding to the immunoblot from the muscle tissue samples of the individual for whom diagnosis is sought is compared to the extent of antibody binding to an otherwise identical immunoblot prepared from a muscle tissue sample from a normal individual, wherein a substantial reduction in the extent of antibody binding to the α7A integrin protein in the immunoblot of the sample from the individual for whom diagnosis is sought as compared to the antibody binding in the immunoblot for the muscle tissue sample from a normal individual is indicative of SPMD. Desirably, the muscle tissue samples are from skeletal muscle. As above, laminin levels are desirably assessed, and in SPMD, those levels are about the same as in a normal individual.

Reverse transcriptase-polymerase chain reaction (RT-PCR) can also be carried out on muscle tissue samples from an individual for whom a diagnosis is sought. RNA is extracted with precautions for preservation of messenger RNA in the samples. The primers noted hereinbelow or other primers which result in the production of an amplification product characteristic in size of the α7A integrin messenger RNA are used. Alternatively, Northern hybridization can be carried out on RNA samples from muscle tissue specimens with probes characteristic of the α7A transcript. SPMD is characterized by reduction in the expression of α7A integrin while levels of 2/4 laminin expression are normal. The primers disclosed herein can be used in the general procedure as disclosed in Hayashi et al. (1998).

BRIEF DESCRIPTION OF THE DRAWINGS

FIG. 1A: The α7BX2 transgene (tg) was detected by PCR using primers that amplify between the MCK promoter and the α7 cDNA sequence. Lanes 2 and 3 are positive for the MCK-α7BX2 transgene. FIG. 1B: Southern analysis using a rat α7 specific probe of EcoRI and KpnI digested genomic DNA. The 7.1 kb band corresponding to the rat transgene construct is detected in lanes 4, 5 and 6. A higher 14.2 kb transgene dimer was also detected. Samples in these lanes are from mdx/utr (−/−) mice. DNA in lanes 1, 2 and 3 are from non-transgenic mice. FIG. 1C: Determining the status of the utrophin gene by PCR. Only mutant utr alleles are detected in lanes 1 and 4 identifying the utr (−/−) mice. One wildtype (wt) and one mutant allele are amplified in lane 2, identifying a utr (+/−) mouse. Lane 3 is wildtype at both utr loci. FIG. 1D: Determining the status of the dystrophin gene by PCR. The mdx primer set detects the point mutation in the dystrophin gene, whereas the wt primers detect only the wildtype allele. Mouse 2 is wildtype at the dystrophin locus, mouse 3 is heterozygous (mcW+1 and mouse +is mdx. Lane 1 contains no DNA.

FIG. 4A: Western blot showing more α7B is detected in transgenic mice compared to non-transgenic mice whereas α7A is constant. FIG. 4B: The blots were re-probed with anti creatine kinase antibody. The CK levels were used to normalize the amounts of α7A and α7B proteins in each sample. The levels of α7A/CK in both transgenic and nontransgenic mice remained constant. In contrast, α7B/CK ratio is 2.3 fold higher in the α7BX2 transgenic mice compared to the non-transgenic animal. FIG. 4C: β1D integrin from 8 week hindlimb muscle. Less β1D is detected in mdx/utr (−/−) mice compared to α7BX2-mdx/utr (−/−) mice. An increase of approximately 1.5-fold more β1D was detected in the transgenic vs non-transgenic mice.

DETAILED DESCRIPTION OF THE INVENTION

Mutations in the α7 integrin gene resulting in the absence or reduction of the α7 integrin protein have been shown to be reasonable for the myopathy and delayed motor milestones Japanese patients with previously undefined muscular dystrophies (Hayashi et al., 1998). In addition, expression of the α7β1 integrin protein has been shown to be up-regulated in Ducheme muscular dystrophies (DMD) and down-regulated in laminin-2/4 (α2β1γ1)-deficient patients. Because of the role of the α7β1 integrin in muscle development, structure and function, we have further examined of its involvement in human muscle disease. Laminin-2/4 is also known as merosin. The structural gene encoding the α7 integrin has been mapped by fluorescence in situ hybridization (FISH) and radiation hybrid mapping to human chromosome 12q13. Given the genetic localization of the SPMD to 12q13-15 and the role of the α7 protein in muscle development and function, we have concluded that lack of expression of this gene is the underlying cause of this progressive wasting disease.

Because of the diminished physical capacities and the early death of muscular dystrophy patients, especially Duchenne muscular dystrophy patients, there is a strong need for effective treatment of these individuals. Successful treatment has humanitarian advantages, as well as economic benefits to society and to families of affected individuals. It has been discovered that expression of the integrin polypeptide α7BX2 in muscle cells at greater than normal levels results in improved function and lifespan in the animal model for Duchenne muscular dystrophy (the mdx/utr-(−/−) mouse). Treatment of human patients with genetic material containing a similarly regulated coding sequence for the integrin polypeptide α7BX2 results in improved physical condition and mobility as well as increased lifespan.

To confirm that the α7β1 integrin linkage system can alleviate severe muscle disease, transfenic mice were produced that express that rat α7 chain in a genetic background which resulted in the absence of dystrophin and utrophin. DNA encoding the rat α7 integrin α7BX2 isoform, under the transcriptional control of the mouse muscle creatine kinase (MCK) promoter, was cloned and shown to have biological activity in vitro (Burkin et al., 1998). The 3.3 kb MCK promoter limits transcription to differentiated skeletal and cardiac muscle, confirming the effects of overexpression to these tissues (Donoviel et al., 1996). The 7.1 kb construct, MCK-α7BX2, was used to express the rat integrin in mdx/utr (−/−) mice. Due to the mortality of the double knockout mice, that rat transgene was initially introduced into a heterozygous [mdx/utr (+/−)]background and these animals were then bred to produce double knockout transgenic offspring. The ratio of offspring followed expected Mendelian genetics indicating the transgenic expression of the rat α7 integrin did not have an obvious effect on embryonic development.

Figure 1:
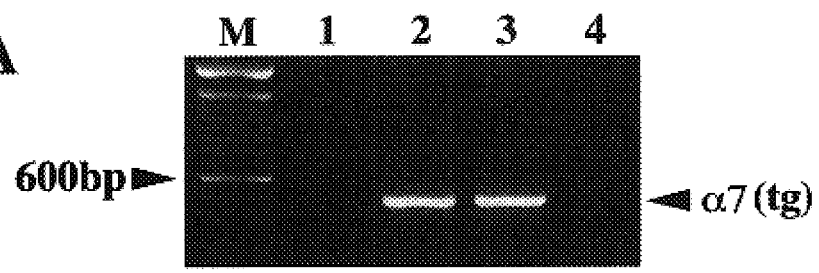
FIGS. 1A–1D illustrate the genotype of transgenic α7BX2-mdx/utr (−/−) mice.
Figure 1:
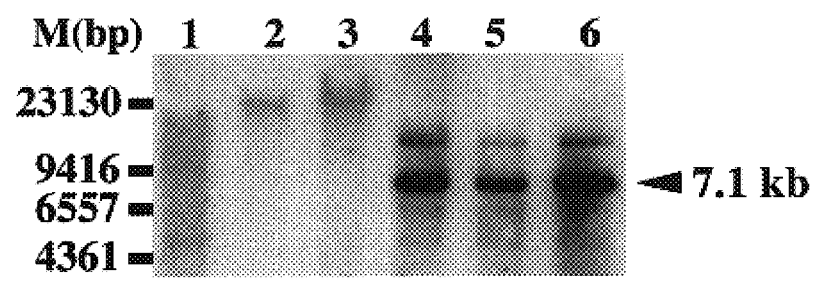
Figure 1:
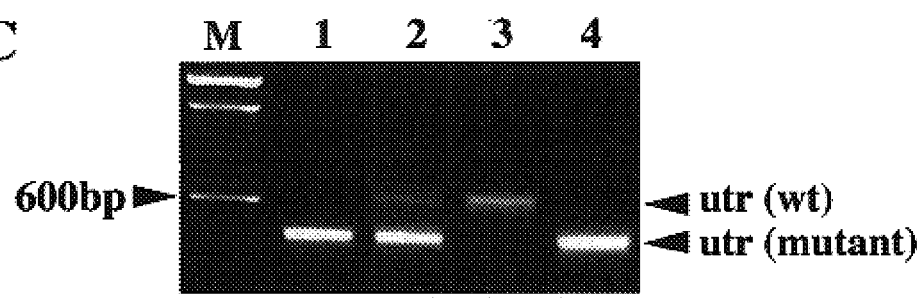
Figure 1:
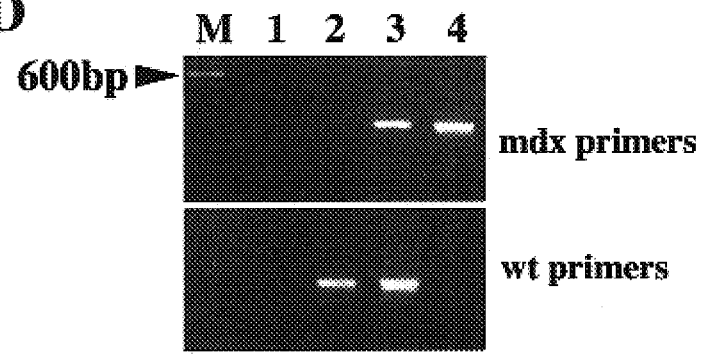

The presence of the rat α7 transgene was detected by both PCR and Southern analyses. Using MCKI and ATTH primers, a 455 bp product was amplified only in transgenic mice (FIG. 1A). Southern analysis produced a strong 7.1 kb band only in transgenic mice. This is the expected size of the EcoRI and KpnI digested MCK-α7BX2 construct (FIG. 1B). A weak 14.2 kb band was also detected by Southern analysis suggesting a portion of the constructs had lost one of these restriction sites.

The status of the utrophin gene was analyzed by PCR using the primers 553, 554 and 22803 previously described (Grady et al., 1997a). A 640 bp product is amplified when the wildtype utrophin allele is present, whereas a 450 bp product is amplified when the utrophin mutant allele is present (FIG. 1C).

The status of the dystrophin gene was determined by the amplification resistant mutation detection system (Amalfitano and Chamberlain, 1996). Using the mdx-specific primer set, a 275 bp mutant allele is detected, while in separate reactions the wild type specific primer set detected a 275 bp wildtype allele. FIG. 1D shows three different genotypes at the dystrophin locus. Mouse 2 is wildtype at the dystrophin locus, mouse 3 is heterozygous (mdx −/+) while mouse 4 is mdx.

Figure 2:
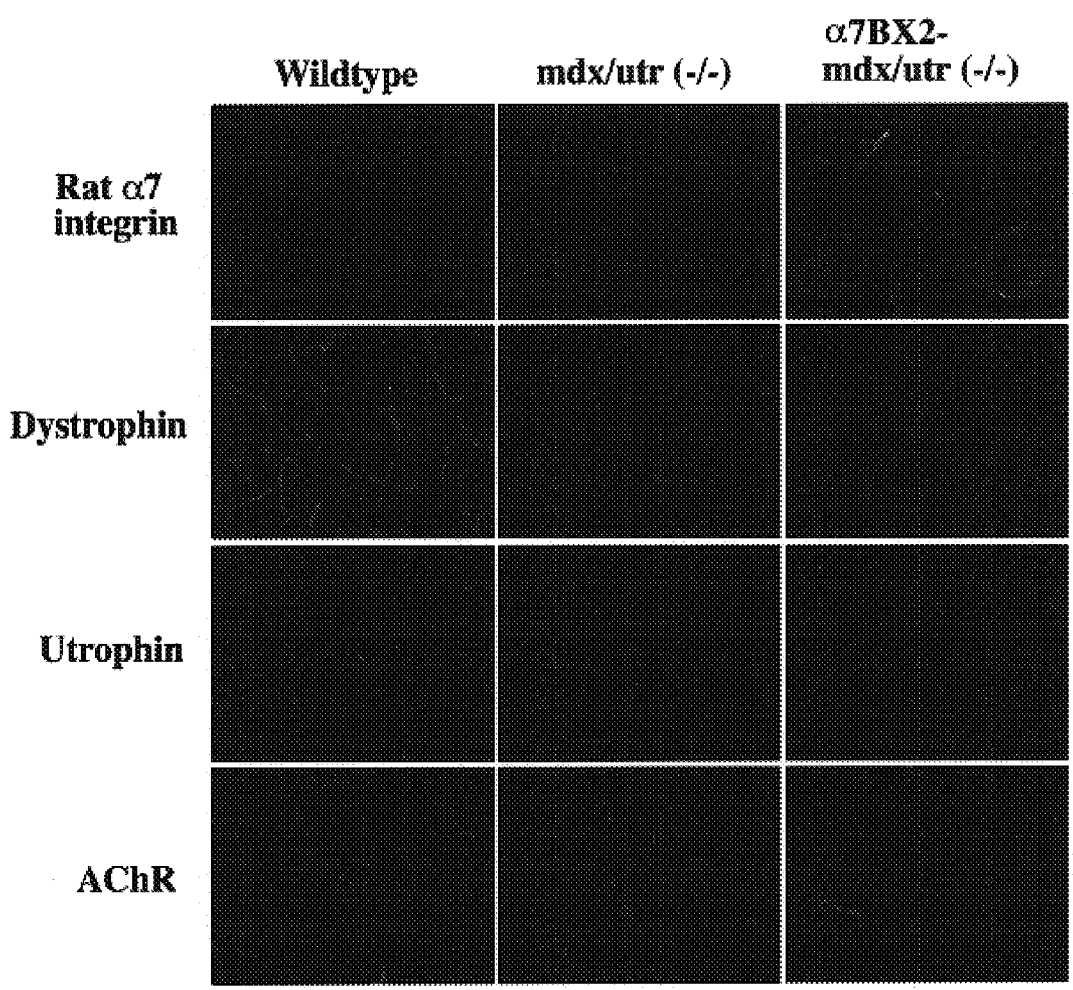
FIG. 2 demonstrates the expression of the rat α7 protein in mouse muscle. Immunofluorescence analysis of hindlimb cryosections using monoclonal antibodies against the rat α7 integrin chain, dystrophin, and utrophin. AChRs were stained with rhodamine-labeled α-bungarotoxin. The rat α7 protein is only detected in transgenic mice and localizes to the membrane of muscle fibers. The lack of dystrophin and utrophin in both transgenic and non-transgenic mdx/utr (−/−) mice confirms their genotypes.

Protein expression from the rat α7 chain transgene was determined by immunofluorescence analysis of cryosections using the rat-specific α7 monoclonal antibody 026 (FIG. 2). The rat α7 chain was only detected by immunofluorescence in the muscle of transgenic mice (FIG. 2). Immunofluorescence also showed the absence of dystrophin in muscle fibers and the absence of utrophin at neuromuscular junctions in both transgenic and non-transgenic mdx/utr (−/−) mice (FIG. 2).

Figure 3:
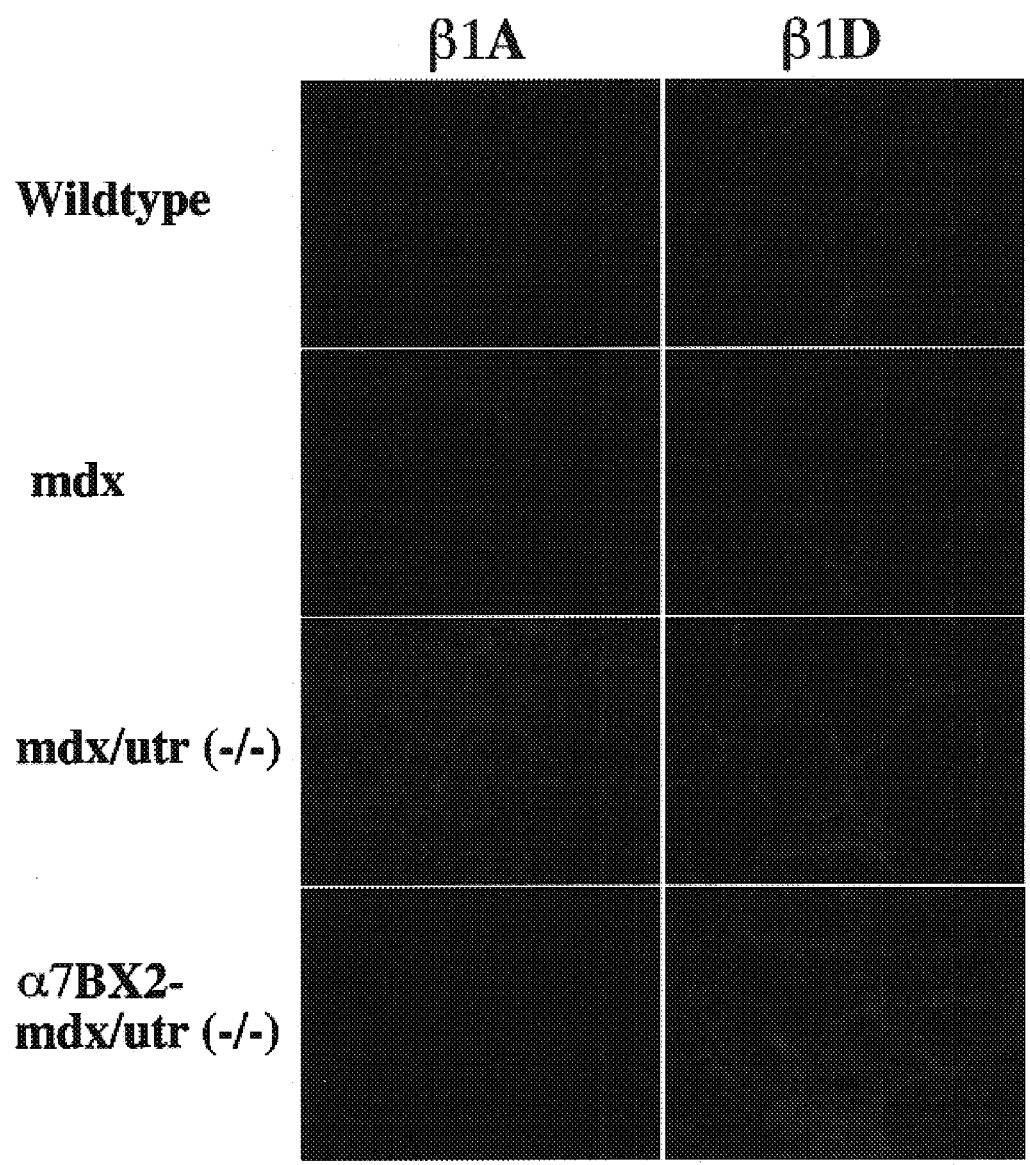
FIG. 3 illustrates the immunofluorescence of β1 integrin isoforms in the hindlimb of 8 week wildtype, mdx/utr (−/−) and α7BX2-mdx/utr (−/−) mice. β1A integrin is elevated in muscle fibers of mdx/utr (−/−) mice compared to wildtype and mdx animals. In contrast, β1A levels are normal in α7BX2-mdx/utr (−/−) mice. Compared to wildtype, an increase in β1D is detected in both mdx and mdx/utr (−/−) muscle α7BX2-mdx/utr (−/−) mice show an additional increase in β1D compared to both mdx and mdx/utr (−/−) mice.
Figure 4A:
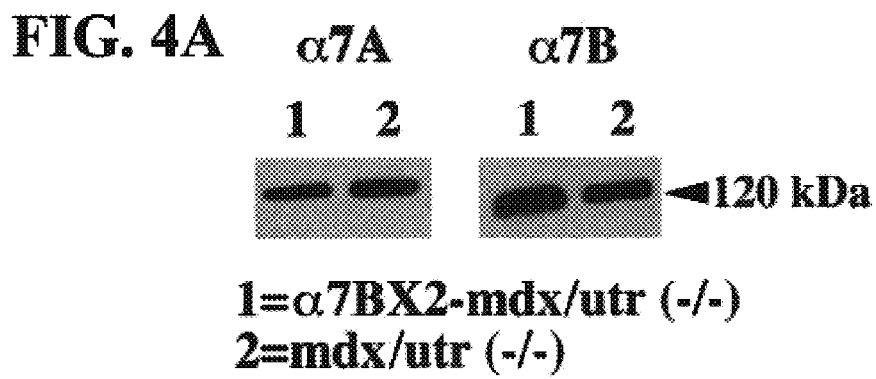
FIGS. 4A–4C show the transgenic expression of α7BX2 increases the amount of β1D in hindlimb muscle.
Figure 4B:
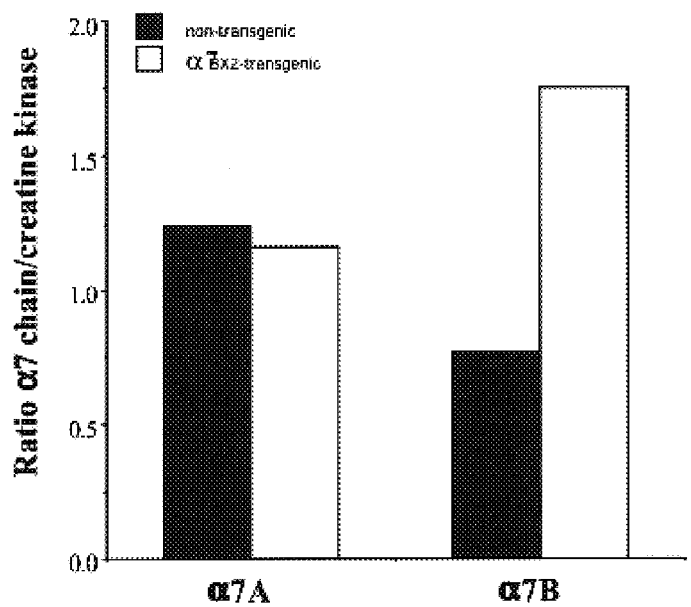
Figure 4C:
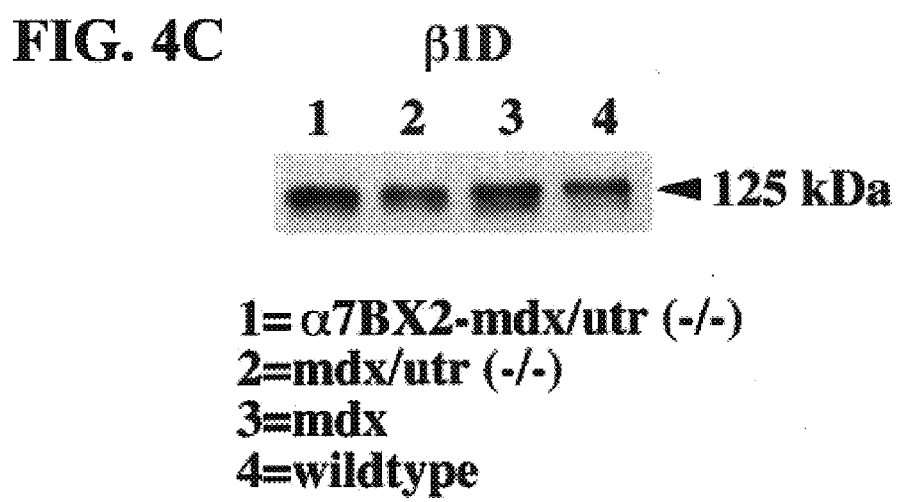

The alternative spliced form of the β1 integrin chain, β1D, is expressed in differentiated skeletal and cardiac muscle (Zhidkova, et al., 1995, van der Flier, et al., 1995; Belkin, et al., 1996;). Compared to the β1A, β1D may form stranger linkages between the cell cytoskeleton and extracellular matrix (Belkin et al., 1997). Immunofluorescence analysis showed β1A levels were elevated in fibers of mdx/utr (−/−) mice contained to wildtype and mdx animals. This is indicative of muscle that is not fully differentiated. In contrast α7BX2-mdx/utr (−/−) mice had normal levels of β1A integrin. Immunofluorescence and western blot analysis showed that mdx and mdx/utr (−/−) mice have more cell surface β1D chain than wildtype mice. This increase in β1D coincided with an increase in endogenous α7 chain in non-transgenic mdx and mdx/utr (−/−) mice as well total α7 in α7BX2-mdx/utr (−/−) mice. The α7BX2 mdx/utr (−/−) mice also had an additional 1.5-fold more β1D compared to mdx/utr (−/−) mice (FIGS. 3 and 4C). Thus an increase in the α7BX2β1D integrin is promoted by increased expression of the α7 transgene expressed specifically in muscle cells.

Figure 5:
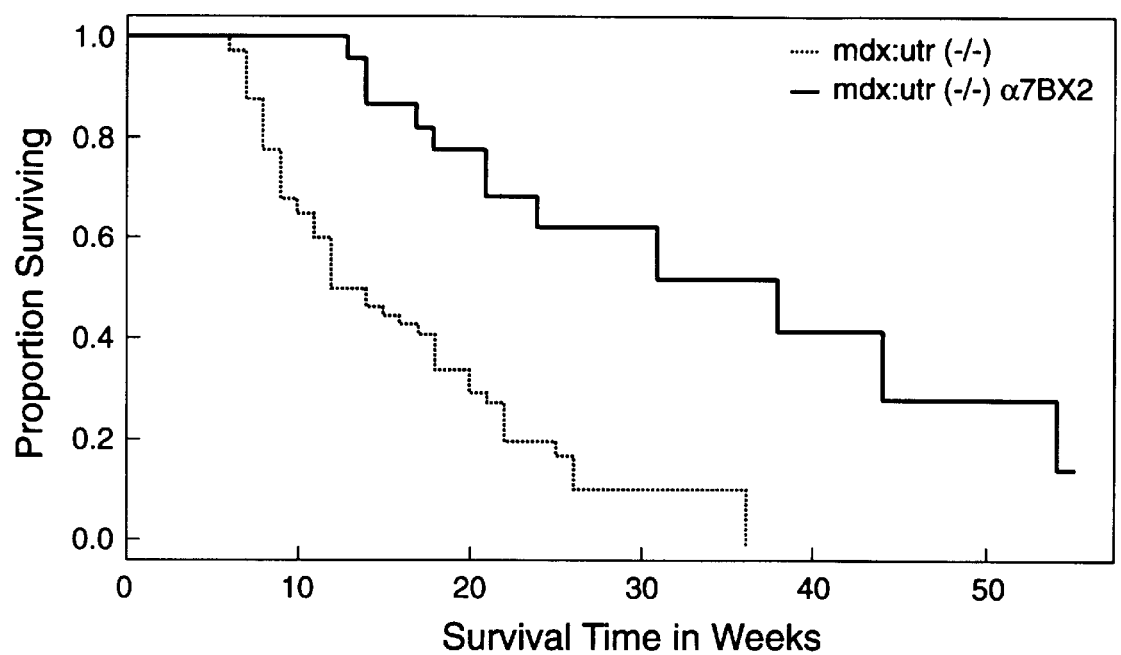
FIG. 5 provides Kaplan-Meier survival curves of 43 α7BX2-mdx/utr (−/−) and 84 mdx/utr (−/−) mice. Wilcoxon and Log rank tests show the α7BX2-mdx/utr (−/−) mice and mdx/utr (−/) populations have distinct survival curves (P<0.001). The α78X2-mdx/utr (−/−) mice survive a 3-fold longer than non-transgenic mdx/utr (−/−) mice with a median life expectancy of 38 weeks in contrast, non-transgenic mdx/utr (−/−) mice have a median life expectancy of just 12 weeks. 95% confidence intervals are indicated by shading.

As previously reported, mdx mice express approximately two-fold more α7 integrin mRNA than wildtype controls (Hodges et al., 1997). No further increase in α7 protein was detected in the mdx/utr (−/−) animals. The amount of α7BX2 protein in the α7BX2-mdx/utr (−/−) mouse hindlimb detected by western blots was approximately 2.3 fold greater than the endogenous α7BX2 chain in mdx/utr (−/−) mice (FIGS. 4A and 4B). As expected, the levels of α7AX2 were equivalent in the transgenic and non-transgenic mice.

α7BX2-mdx/utr (−/−) mice exhibit increased longevity and mobility as compared to the mdx/utr (−/−) mice. Longevity was significantly extended in the α7BX2-mdx/utr (−/−) transgenic mice (FIG. 5). Kaplan-Meier survival analysis (Kaplan and Meier, 1958) of 84 non-transgenic and 43 transgenic mdx/utr (−/−) mice demonstrated that the observed differences in survival of these populations were statistically significant (p<0.001). Log-rank (Peto et al., 1997) and Wilcoxon rank-sum tests (Conover, 1980) showed that the difference in survival emerged soon after birth and was maintained throughout the observed lifetime of the animals. The mdx/utr (−/−) mice used in these experiments developed severe muscular dystrophy and 50% died before 12 weeks of age. The median age at death of the transgenic mdx/utr (−/−) mice was 38 weeks, a three-fold increase over that observed in non-transgenic mdx/utr (−/−) littermates. These findings were similar in male and female mice. The oldest α7BX2-mdx/utr (−/−) mouse was sacrificed at 64 weeks of age.

Figure 6:
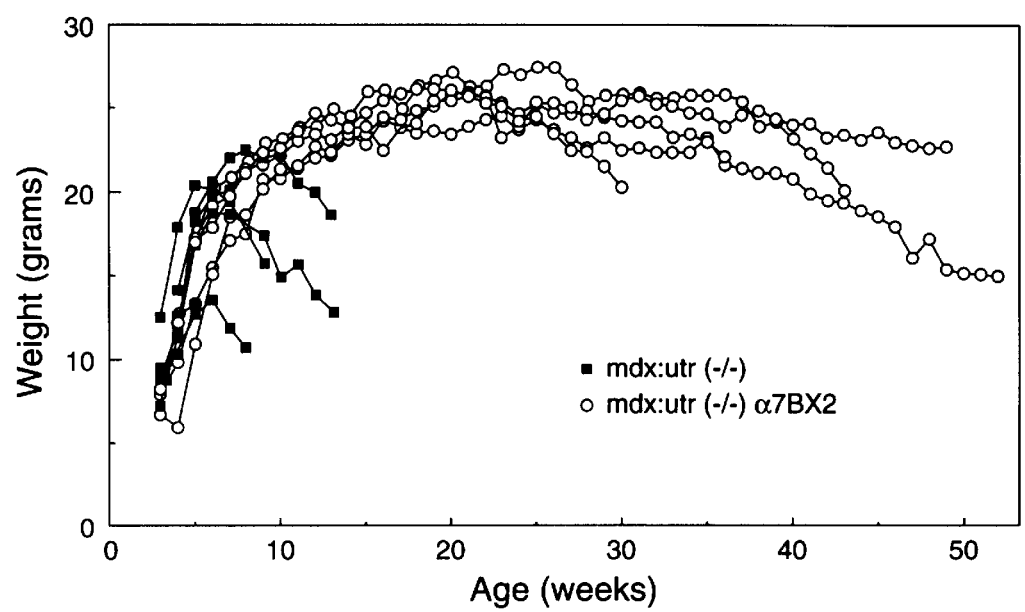
FIG. 6 illustrates weight gain vs survival in representative mdx/utr (−/−) mice and α7BX2-mdx/utr (−/−) mice. The majority of non-transgenic mdx/utr (−/−) mice undergo a crisis at 5–10 weeks of age that results in a sudden loss of weight and premature death. Most transgenic mdx/utr (−/−) mice live longer and maintain weight. Eventually these also go through a crisis that results in weight loss.

Compared to mdx mice that exhibit minimal pathology, mdx/utr (−/−) mice do not maintain weight. Instead these mice undergo a crisis product that results in weight loss and premature death at 8–20 weeks of age (Grady, et al., 1997b; Deconinck, et al., 1997b). In contrast, α7BX2-mdx/utr (−/−) transgenic mice did not show sudden weight loss. Animal weight stabilized between 20–25 grams (FIG. 6). No significant differences were found in the weights of mdx mice compared to α7BX2-mdx mice between 3 to 30 weeks of age. Thus, extra α7BX2 chain itself does not promote weight gain.

By 8 weeks of age mdx/utr (−/−) mice exhibited limited mobility and a waddling gait. In contrast, α7BX2-mdx-utr (−/−) littermates had highly improved mobility, comparable to mdx mice. The transgenic mice are dramatically improved in parameters including kyphosis, gait, joint contractures and mobility, as compared with the mdx/utr (−/−) mice lacking the transgene.

Figure 7:
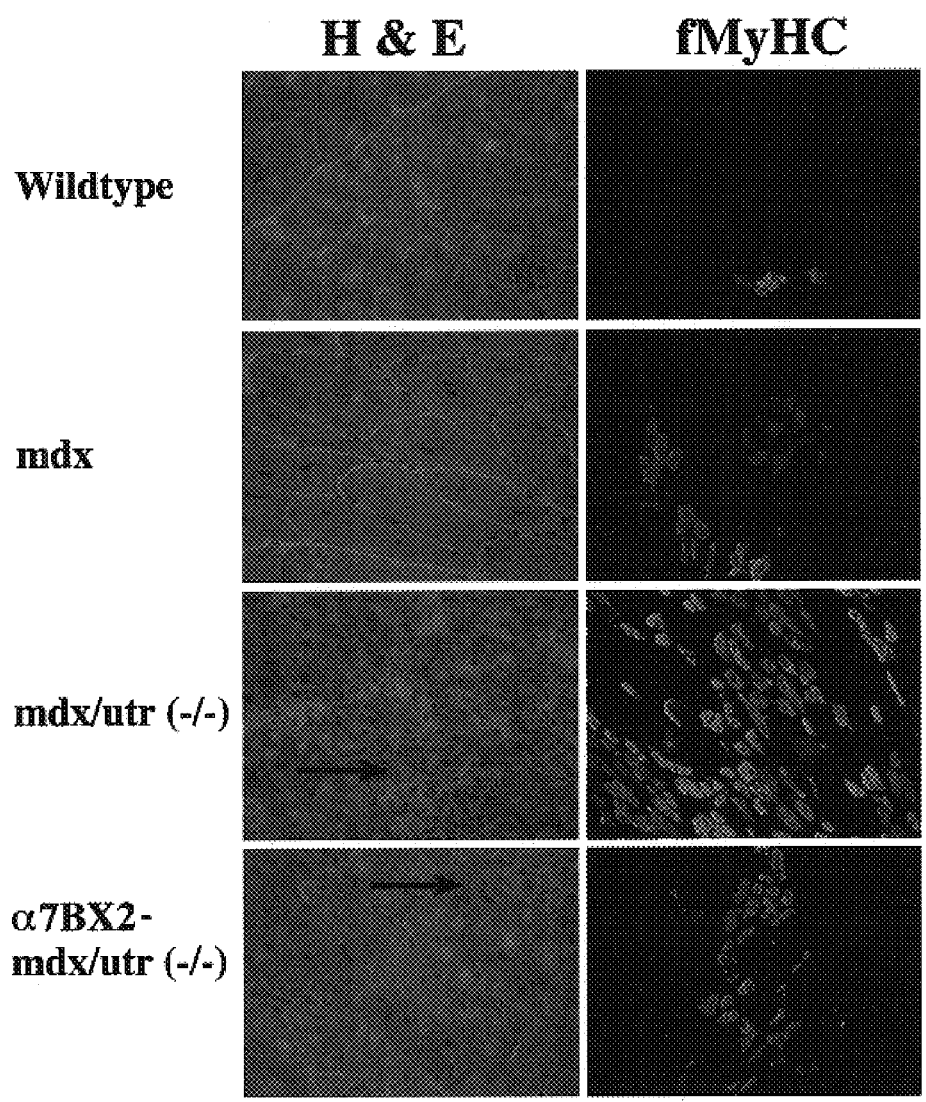
FIG. 7 shows histology of hindlimbs from 10 weeks wildtype, mdx. mdx/utr (−/−) and αBX2-mdx/utr (−/−) mice. Hematoxylin and eosin staining reveal abundant central nuclei in mdx, mdx/utr (−/−) and α7BX2-mdx/utr (−/−) mice. Mononuclear cell infiltration and expression of fMyHC are extensive in the mdx/utr (−/−) mice, but are reduced in the α7BX2-mdx/utr (−/−) transgenic animals, indicating less degeneration and more stable regeneration in these mice.

Enhanced expression of the α7BX2 chain stabilizers regeneration in mdx/utr (−/−) mice. Nuclei are normally localized along the periphery of myofibers, whereas in regenerating muscle nuclei are centrally located (DiMario, et aL. 1991). Regeneration is also accompanied by a transient reversion to expression of fetal isoforms of myosin heavy chain (fMyHC) (Matsuda, et al., 1983; Sand, et al., 1987). Hindlimb sections from 5, 8 and 10 week old wildtype, mdx, mdx/utr (−/−) and α7BX2-mdx/utr (−/−) mice were stained with hematoxylin and cosin to determine the extent of mononuclear infiltration and centrally located nuclei (FIG. 7 and Table 1). Immunofluorescence of fMyHC was also determined. Degeneration and regeneration that are characteristic of muscle disease occur earlier in mdx/utr (−/−) animals compared to mdx mice (FIG. 7 and Table 1). These results are consistent with the earlier onset of necrosis and cell infiltration previously reported in these animals (Grady et al., 1997b; Deconinck et al., 1997b). The occurrence of central nucleii in α7BX2-mdx/utr (−/−) mice was similar to that in mdx/utr (−/−) mice indicating that enhanced expression of the integrin does not prevent early degeneration and regeneration. Likewise, fMyHC expression was most extensive at 5 weeks in the mdx/utr (−/−) and α7BX2-mdx/utr (−/−) mice. In contrast, mdx mice exhibited very little fMyHC at 5 weeks. At 8 weeks fMyHC was elevated in mdx mice and at 10 weeks it was reduced, indicating that a cycle of degeneration and regeneration was followed by stabilization. The shift from the 1A to β1D chain supports this conclusion. At all ages examined, the extent of fMyHC expression in the α7BX2-mdx/utr (−/−) animals was intermediate between that found in the mdx and mdx/utr (−/−) animals. In the 8 and 10 week old transgenic mdx/utr (−/−) mice, fMyHC expression approached that in mdx mice (FIG. 7). This decreased expression of fMyHC in a α7BX2-mdx/utr (−/−) mice paralleled the greater integrity of tissue seen in the 8 and 10 week transgenic animals compared to the mdx/utr (−/−) mice. The extensive mononuclear cell infiltration observed in the mdx/utr (−/−) mice was also partially reduced in the α7BX2 mdx/utr (−/−) animals (FIG. 7). Thus, enhanced expression of the α7β integrin does not alter the initial degenerative cycle, but once regeneration has taken place, the additional integrin appears to stabilize muscle integrity reducing muscle pathology.

Figure 8:
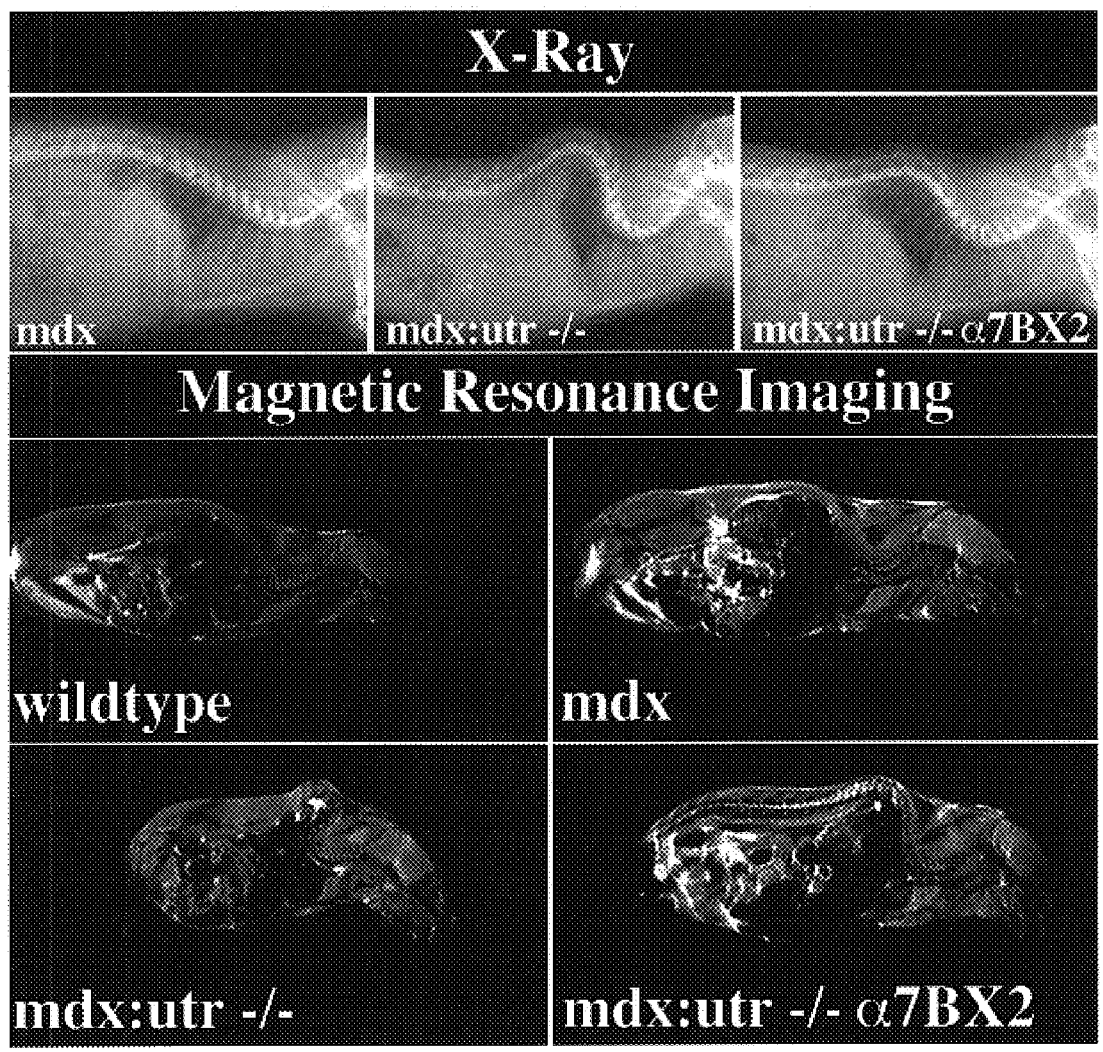
FIG. 8 shows the results of X-ray and magnetic resonance imaging of normal and dystrophin mice. Upper panels: the severe spinal curvature (kyphosis) and constriction of the rib cage in mdx/utr (−/−) mice are largely reduced in the α7BX2 transgenic animals. Lower panels: MRI of mid-sagittal sections reveal kyphosis and reduction of pulmonary volume in mdx/utr (−/−) mice are largely alleviated in transgenic mice.

Kyphosis and joint contractures are alleviated in α7BX2-mdx/utr (−/−) mice as compared with the mdx/utr (−/−) mice. Severe curvature of the spine (kyphosis) in DMD patients and mdx/utr (−/−) mice is due to a failure of the muscles that would normally support the spinal column (Oda et al., 1993). X-ray images showed that both kyphosis and rib cage compression were markedly reduced in α7BX2-mdx/utr (−/−) mice compared to mdx/utr (−/−) littermates (FIG. 8). This was confirmed by whole body magnetic resonance imaging (MRI) which visualized not only the tissues surrounding the spinal column, but bundles of muscle fibers, the heart, lung and other soft tissues. The reduction in kyphosis promoted by the enhanced expression of integrin in the α7BX2-mdx/utr (−/−) animals likely is a major factor in their survival. Kyphosis results in the diaphragm being pushed forward, compromising lung capacity and diaphragm function, and thereby contributing to cardiopulmonary failure. A partial reduction of kyphosis has dramatic effects on survival.

Figure 9:
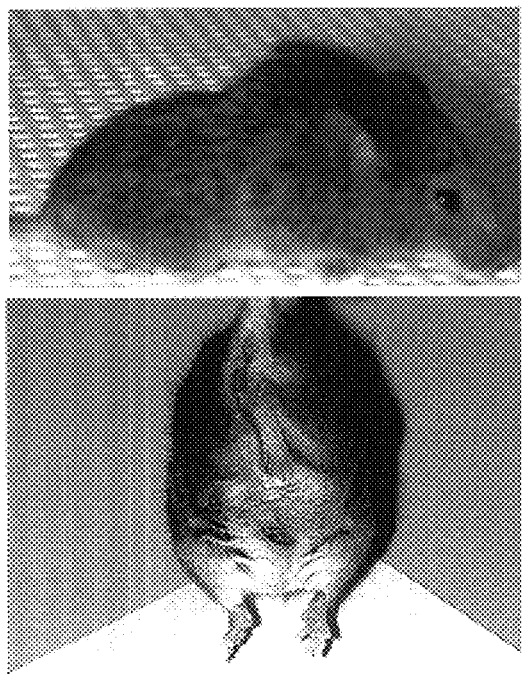
FIG. 9 show that severe spinal curvature (kyphosis) and hindlimb clasping (joint contractures) are largely reduced in mice expressing the rat α7BX2 transgene.
Figure 9:

A hallmark of diseased musculature is the failure to extend limb muscles, resulting in joint contractures and impaired mobility. Hindlimb joint contractures are conspicuous in mdx/utr (−/−) mice but are markedly reduced in the α7BX2-mdx/utr (−/−) mice (FIG. 9). The reduction in hindlimb joint contractures allows the mice to have greatly improved mobility.

Structural changes from the normal patterns in the neuromuscular junctions of α7BX2-mdx/utr (−/−) mice are reduced due to the expression of the integrin chain. The neuromuscular junctions (NMJs) in utr (−/−) mice exhibit a significant reduction the numbers of synaptic folds, and density of AchRs (Grady et al., 1997a; Deconinck et al., 1997a). This is exacerbated in mdx/utr (−/−) mice that show even greater reductions in post-synaptic folding and AChR density (Grady et al., 1997b; Deconinck et al., 1997b). The post-synaptic plate of the NMJ in the mdx/utr (−/−) mice appears en face as discrete boutons rather than as a continuous folded NMJ structure (Grady et al., 1997b; Rafael et al., 2000).

Figure 10:
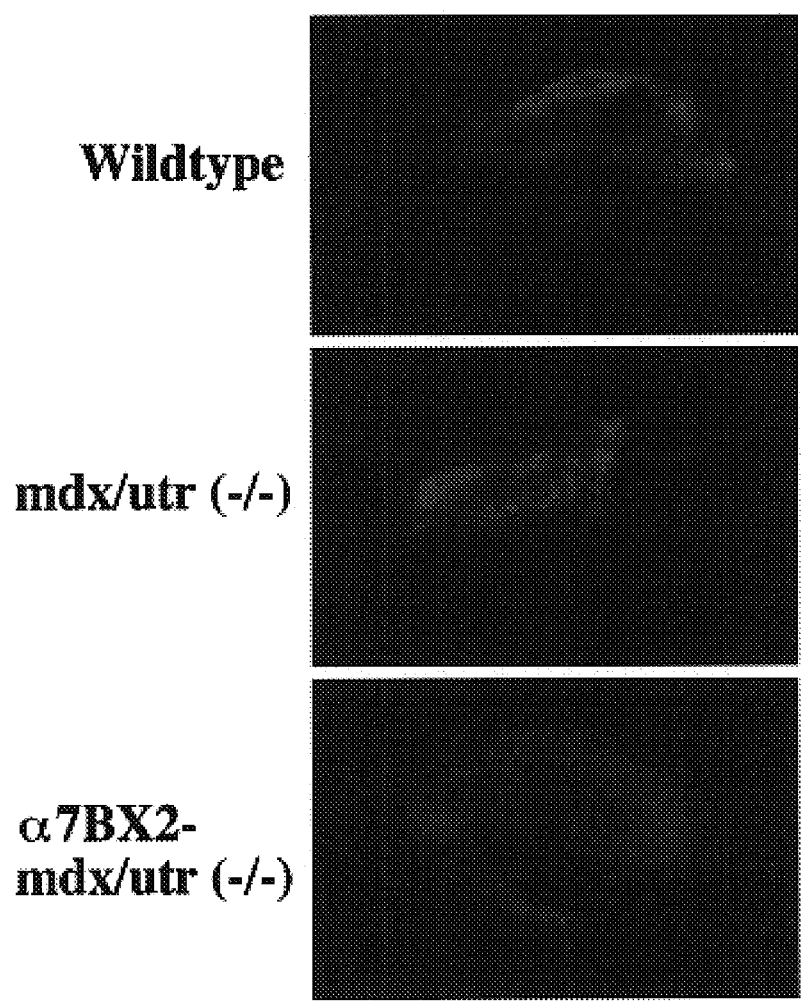
FIG. 10 provides en face images of neuromuscular junctions of 8 week wildtype, mdx/utr (−/−) and α7BX2-mdx/utr (−/−) mice. Localization of acetylcholine receptors (AChRs) in the postsynaptic membrane of wildtype mice, detected with rhodamine-labeled α-bungarotoxin, is continuous and uninterrupted. In contrast, mdx/utr (−/−) mice have discontinuous distributions of AChRs organized into discrete "boutons". The organization of the postsynaptic membrane in α7BX2-mdx/utr (−/−) transgenic mice has a more continuous (normal) en face pattern.

Because the α7β1 integrin is normally found at NMJs (Martin et al., 1996) and participates in the clustering of AChRs in C2C12 cells (Burkin et al., 1998, 2000), we compared the structure of NMJs from 8 week old wildtype, mdx/utr (−/−) and α7BX2-mdx/utr (−/−) mice (FIG. 10). Longitudinal sections from the hindlimb muscle were stained with rhodamine-labeled α-bungarotoxin and images of en face sections of the postsynaptic membrane were analyzed. Immunofluorescence staining of the NMJs of mdx/utr (−/−) mice appeared less intense than those of wildtype mice and showed extensive discrete boutons. In contrast, most NMJs from α7BX2-mdx/utr (−/−) mice appeared more continuous. Thus, enhanced levels of the α7β1 integrin help maintain the normal structure of the NMJ.

Our results demonstrate, for the first time, that enhanced expression of the α7β1 integrin can alleviate the development of muscular dystrophy and significantly extend longevity. Mice lacking both dystrophin and utrophin were used in this study because in the absence of both proteins, direct substitution of dystrophin with utrophin is precluded. This results in the development of severe muscular dystrophy and premature death, symptoms that closely resemble those seen in Duchenne muscular dystrophy (Grady et al., 1997b, Deconinck, et al., 1997b), an important muscular dystrophy in humans.

The α7BX2-mdx/utr (−/−) mice reported here have approximately 2.3-fold more α7BX2 chain than their non-transgenic littermates. The β1D chain, partner to α7, is also increased in the α7BX2 transgenic mice. The increased levels of α7β1 ingegrin led to a three-fold extension in median survival time, markedly improved mobility, and reduced kyphosis and joint contractures in the transgenic mdx/utr (−/−) mice. Kaplan-Meier survival analysis of the transgenic and non-transgenic mdx/utr (−/−) mice shows that the extension of longevity due to expression of the transgene is statistically significant and is evident early and throughout the life of the animals.

The survival times of the mdx/utr (−/−) mice in these experiments differ slightly from those previously reported. The original reported longevity of the mdx/utr (−/−) used to produce the animals in our experiments was 4–14 weeks (Grady, et al., 1997b). More recently, a life span of 4–20 weeks has been reported (Grady et al., 1999) and occasional longer living mice have been noted by others. We too have noted some "outliers" in that 6 of 84 mdx/utr (−/−) mice survived beyond 22 weeks, with the oldest mouse drying at 36 weeks of age. The transgenic and non-transgenic mice with extended life spans were re-evaluated for expression of dystrophin and utrophin by PCR and immunofluorescence and were again found deficient in both. Nevertheless, α7BX2-mdx/utr (−/−) mice are clearly distinct in longevity, mobility and histology from nontransgenic littermates. The median lifespan of the α7BX2-mdx/utr (−/−) mice was 38 weeks whereas the median life span for those not receiving the transgene was 12 weeks of age.

Electron microscopy has been used to compare the NMJs and myotendinous junctions of mdx/utr (−/−) and α7BX2-mdx/utr (−/−) mice. The normal field morphology of the post synaptic membrane of then NMJ that is severely compromised in the mdx/utr (−/−) mice is largely maintained where there is increased expression of the α7BX2 integrin. Similarity, the normal folding of the myotendinous junction that is absent in the severely dystrophic mice is also maintained when the levels of the a7β1 integrin are increased. Thus, morphology of those structures that are involved in initiating muscle contraction and generating force and movement are preserved by enhanced expression of the integrins. Without wishing to be bound by any particular theory, the present invention believes that the maintenance of the structure and function of both the myotendinous junction and neuromuscular junctions contributes to the increase in the lifespan of the transgenic mice.

Enhanced expression of integrin prevents development of cardiomyopathy. The elevation of atrial natiurectic factor (ANF) seen in dystrophic mdx/utr (−/−) mice (and in dystrophic humans) is largely alleviated in animals expressing elevated levels of the α7β1 integrin. Likewise, uptake of Evans blue, an indicator of membrane damage, and histologic determination of lesions in the heart all indicate that cardiomyopathy is largely reduced in the α7BX2-mdx/utr (−/−) mice as compared with the double knockout animals. Thus, enhanced expression of the integrin significantly prevents the development of pathology in both skeletal and cardiac muscle and it alleviates then symptoms in humans or animals suffering from the symptoms of dystrophy.

Although the mechanism by which enhanced expression of the α7 integrin protein alleviates the development of the dystrophin deficient phenotype is not currently understood, multiple effects that result from additional α and β integrin chains are possible. An added advantage of the α7BX2 integrin expression is that it is a protein produced in the muscular dystrophy patients, and therefore, there is no potential for an immune reaction to it as there would be in the recombinant expression of a protein which is not already expressed in those patients.

Suitable vectors for directing the expression of the α7BX2 integrin expression include retrovirus vectors, adenovirus vectors and adeno-associated virus vectors. Vectors and methods are described in references including, but not limited to, Campeau et al. (2001); Stedman, H. (2001); Yoon and Lee (2000); Wang et al. (2000), Ragot et al. (1993). Muzyczka, N. (1992), Greelish et al. (1999), Xiao et al. (2000), Cordier et al. (2000), Ascadi et al. (1996), Gilbert et al. (1999), Ebihara et al. (2000), Fujii et al. (2000), Poirier et al. (2000).

Expression of the β1D chain is, in nature, restricted to differentiated skeletal and cardiac muscle (Zhidkova, et al., 1995, van der Flier, et al., 1995; Welkin, et al., 1996; Welkin et al., 1997). In contrast, the β1A chain is present in a wide variety of cell types including myogenic precursor cells. The β1D cytoplasmic domain acts to arrest the progression of myoblast proliferation, alter subcellular localization and affinity of α7β1 for its ligand, and alter the association of the α7β1 with the cell cytoskeleton (Welkin et al., 1997).

Increased β1D expression in α7BX2 transgenic mice appears to increase the interaction between the extracellular matrix, sarcolemma and the cell cytoskeleton, stabilizing muscle integrity. Moreover, β1A, characteristic of non-muscle cells and undifferentiated muscle, is increased in mdx/utr (−/−) and decreased in the transgenic mdx/utr (−/−) animals. The shift from β1A and increased β1D reflects less mononuclear cell infiltrates and increased stability of muscle fibers in the rescued mice.

The α7BX2 integrin chain is normally concentrated at neuromuscular and myvotendinous junctions (Martin et al., 1996), as well as at intrafascicular junctions. In patients with Duchenne muscular dystrophy and in mdx and mdx/utr (−/−) mice, endogenous expression of the α7 integrin protein is increased and the α7BX2 isoform is also found extrajunctionally (Hodges et al., 1997). This increase in expression and re-distribution of α7β1 integrin in dystrophic mice is also seen with utrophin that is normally confined to neuromuscular junctions (Matsumura et al., 1992). Immunolocalization of integrin encoded by the rat α7transgene, detected with anti-rat α7 antibodies, shows that the rat α7 protein is also distributed more globally in the α7BX2-mdx/utr (−/−) animals. Enhanced expression of the integrin therefore contributors to the mechanical integration and stability between muscle fibers and at their junctional sites. Other possible mechanisms may also underlie how the α7β1 integrin rescues mdx/utr (−/−) mice.

Whereas the MCK promoter drives transcription in skeletal and cardiac muscle (Donoviel et al., 1996), enhanced expression of the αβ1 integrin in the heart also contributes to the rescue of these animals. However, expression of utrophin in skeletal muscle, but not cardiac muscle, of mdx/utr (−/−) mice increased survival and reduced pathology (Rafael et al., 1998). These observations suggest that the loss of skeletal muscle integrity is the major factor in the development of muscle pathology in mdx/utr (−/−) mice.

The role of the α7β1 integrin in the formation of the postsynaptic membrane (Burkin, et al., 1998; 2000) suggests that increased integrin expression enhances the development and stability of the NMJ. Dystrophin and utrophin are also concentrated at the postsynaptic membrane and mdx/utr (−/−) and mdx/utr (−/−) mice show progressive alterations of the ultrastructure of these sites (Grady et al., 1997b. Deconinck et al. 1997b). Whereas wildtype and utr (−/−) mice have NMJ endplates that are highly folded and continuous, mdx and mdx/utr (−/−) mice show discontinuous NMJs that are described as discrete "boutons" (Grady et al., 1997a, 1997b; Rafael et al., 2000). Whereas both mdx and utr (−/−) mice show a reduction in the number of synaptic folds when compared to wildtype mice, mdx/utr (−/−) mice show even fewer synaptic folds (Grady et al., 1997b; Deconinck et al., 1997b). Transgenic expression of the α7BX2 chain appears to maintain the normal en face structure of the postsynaptic membrane in mdx/utr (−/−) mice.

In the absence of dystrophin, there is an increase in total muscle calcium (Bertorini et al., 1982) and an elevation of intracellular calcium ($[Ca^{2-}]i$) in isolated dystrophic myofibers (Turner et al., 1988). These increases have been attributed to leaky calcium channels in dystrophic muscle compared to normal muscle. The $[Ca^{2-}]i$ increase may activate $Ca^{2-}$-dependent proteolysis and increase muscle degeneration (Denetclaw et al., 1994). $[Ca^{2-}]i$ levels are also regulated by signaling through the α7β1 integrin (Kwon et al., 2000) suggesting that this integrin may contribute to the maintenance of calcium levels in myofibers. If so, the transgenic expression of the α7BX2 chain may regulate the activity of calcium channels, stabilizing $[Ca^{2-}]i$ levels in mdx/utr (−/−) myofibers and reducing $Ca^{2-}$-dependent proteolysis and muscle degeneration.

Enhanced expression of the α7 integrin may contribute to additional charges in the expression of other proteins, both within the cell and in the extracellular matrix. For example, matrix stability or modeling may potentiate both mechanical and signal transduction capacities of muscle (Colognato et al., 1999). The dual role for the integrin is consistent with analyses of α7(−/−) mice. The myotendinous junctions of fast fibers are compromised in α7 deficient mice (Mayer, et al., 1997). These myofibers also exhibit a partial shift from β1D to β1A integrin and activation of the C-Raf-1)/mitogen-activated protein kinase-2 signaling pathway. These changes cause a reduction of integrin dependent association of fibers and the basal lamina, contributing to the dystrophy that develops in these mice (Saher and Hilda, 1999). As shown herein, increased α7 chain leads to increased β1D integrin.

A broad phenotype is seen in children with congenital muscular dystrophies that arise from mutations in the α7 gene (Hayashi et al., 1998). These patients exhibit congenital myopathy, delayed motor milestones, and severe impairment of mobility. These phenotypes are consistent with a role for α7β1 integrin in the formation and stability of the postsynaptic membrane, myotendinous junctions, and overall stability of muscle integrity.

Since enhanced expression of the α7β1 integrin can alleviate many of the symptoms of severe muscle dystrophy in mdx/utr (−/−) mice, it appears that the integrin-mediated and dystrophin-mediated linkage systems between myofibers and the extracellular matrix are in many ways functionally complementary mechanisms. As such, the enhanced expression of the α7β1 integrin is a novel approach to alleviate Duchenne muscular dystrophy and treat α7 integrin-deficient congenital muscular dystrophies. Moreover, increasing integrin levels proves effective in reducing the development of other muscular dystrophies and cardiomyopathies that arise from compromised expression of other components of the dystrophin glycoprotein complex, but especially those muscular dystrophies in which there is a lower than normal level of α7 integrin protein.

As an alternative to the use of gene therapy to increase α7BX2 expression in the muscular dystrophy patient, one can administer a composition effective for enhancing the level of expression of the patient's own α7BX2 sequence. The present invention provides a methods for screening for enhanced α7BX2 expression: one of ordinary skill in the art can use quantitative (semi-quantitative) reverse transcriptase-polymerase chain reaction (RT-PCR) assays or Northern hybridizations which allow determination of relative amounts of mRNA. Muscle cells or myogenic cells (either normal or derived from a muscular dystrophy patient or from an animal model for same) in culture are treated with test compositions and the amounts of α7BX2 or α7-specific transcripts are determined in response to a test compositions in comparison to a control which has not treated with the test composition. Expression is enhanced in response to the test composition when the level of α7BX2 or α7-specific transcript is greater in the presence than in the absence of the test composition. Alternatively, the amount or relative amount of α7BX2 or other α7 protein is determined after growth of the muscle or myogenic cells in the presence and absence of the test composition. The amount or relative amount can be determined using α7BX2 or α7-specific antibody using any of known immunological assays radioactive immunoassay, western blotting, enzyme-linked immunoassays, sandwich immunoassays and the like. As an alternative to immunological methods, the amount or relative amount of the protein can be determined by the use of muscle or myogenic cells transformed with a fusion protein coding sequence for an α7BX2 protein linked to a green fluorescent protein sequence, other reporters (such as luciferase, β-galactoside, β-lactamase, β-glucuronidase, among others) or an immunological tag portion which can then allow specific immunological measurement of the target fustion protein. Such a fusion protein is expressed under the regulatory control of the native α7 promoter. Compositions identified by any of the assay methods noted above are used in the amelioration of muscular dystrophy symptoms by stimulating or increasing expression of the patient's own gene. Similarly, screening can be accomplished in which increased levels of the polypeptide are detected in response to treatment of the cells with a composition which increases the stability of the α7BX2 protein in the cells. Compositions identified by the screening methods described herein are useful in vivo for the increased expression and/or stability of the α7BX2 protein in muscle cells and for the amelioration of muscular dystrophy symptoms in patients due to a net increase in the α7BX2 protein. Methods for high throughput screening for expression levels or for the amount of a fluorescence-tagged or enzyme-tagged protein are well known in the art, and can be readily adapted to the present measurement of α7BX2 protein without the expense of undue experimentation.

Altered expression of the α7β1 integrin is evident at a relatively high frequency in patients with muscular dystrophies of undefined origin. To determine the extent of involvement of the α7β1 integrin in skeletal muscle diseases, 303 human biopsy samples were screened for expression of both the α7A and α7B isoforms. Of these, 36 patients were totally deficient in both isoforms, whereas the others had anomalous expression of only one isoform of the α7 chain. This indicates that complex regulation of integrin production, or selective stability, underlies certain muscle diseases. The high frequency of involvement of the α7β1 integrin in congenital muscle diseases supports the need for rapid screening and analyses of patients.

To determine if the α7 integrin polypeptide is involved in SPMD, muscle biopsies taken from five patients with SPMD were analyzed for integrin expression. Using immunofluorescence and western blot analyses, it was shown that there was a marked reduction or absence of the α7B integrin in all five SPMD patients as compared with normal healthy controls. In contrast, the α7B integrin was detected in the lining of the blood vessels, suggesting that aberrant tissue specific gene expression or alternative RNA splicing may cause the lack of this integrin in skeletal muscle. Immunofluorescence analysis revealed an increase in levels of dystrophin in muscle fibers of SPMD patient tissue samples; perhaps dystrophin compensates for the reduced integrin linkage system in skeletal muscle. In addition, utrophin expression, normally confined to neuromuscular junctions, was observed throughout the muscle membranes of SPMD patients. Our results indicate that the reduction (or lack) of α7β1 integrin in skeletal muscle contributes to SPMD.

Figure 12:
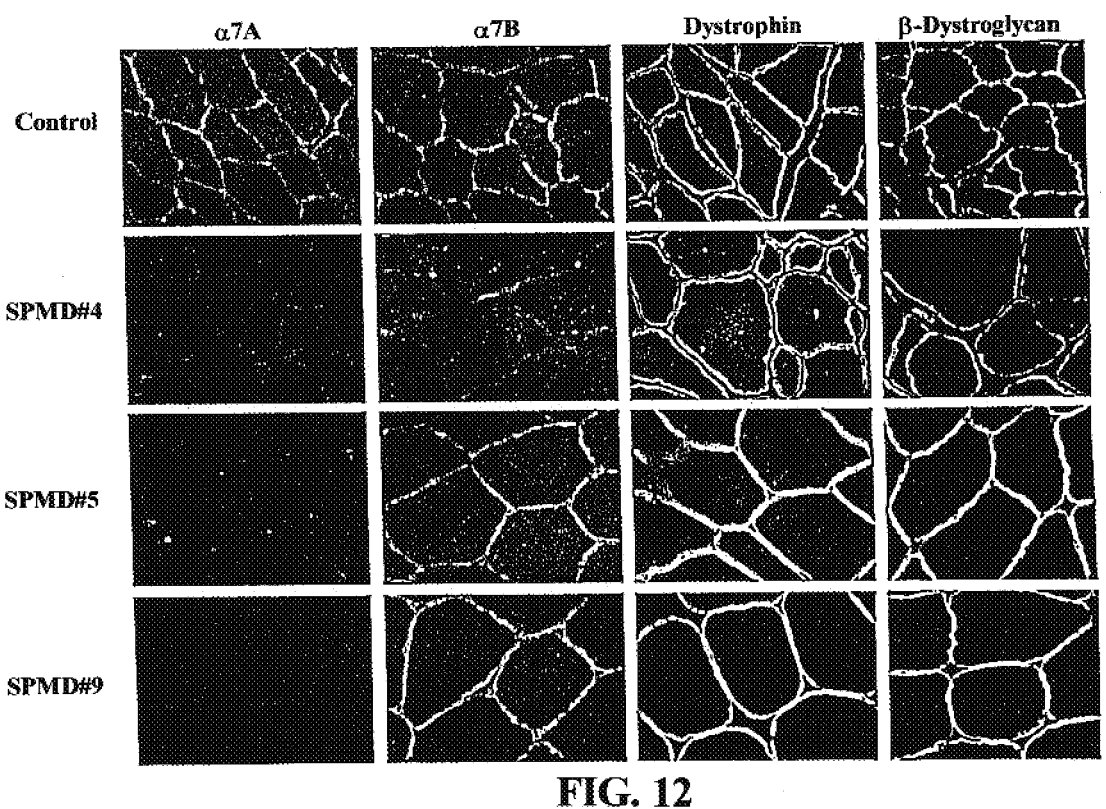
FIG. 12 presents an immunofluorescence analysis of muscle biopsy material from three SPMD patients. The α7A integrin is absent from all three patient samples, and the amount of α7B is decreased in relation to the severity of the pathology in the patients. Interestingly, the amounts of dystrophin and β-dystroglycan, two proteins that comprise an alternative adhesive mechanism, is increased in the SPMD patient biopsy materials.

Cryosections from muscle biopsies from normal individuals and from SPMD patients were initially screened by immunofluorescence using a pan anti-α7 integrin antibody (O26) to detect all integrin isoforms. This antibody was originally developed against the rat α7 protein but at high concentrations (>35 μg/ml), human α7 staining is detected by immunofluorescence. Normal muscle showed typical α7 integrin protein throughout the sarcolemma with higher concentrations at junctional sites. In all SPMD patients whose biopsies were analyzed, little or no α7 integrin protein was detected (FIG. 12). Two other patients (#6 and #7) had such severe pathology that little skeletal muscle was present in the biopsy sample. The muscle fibers present in these patients showed a significant reduction in α7 integrin immunofluorescence signal. Blood vessels in some patients (e.g., #6) showed strong α7 integrin expression (presumably α7B integrin) suggesting integrin loss was restricted to skeletal muscle tissue. To control these experiments, secondary antibody-only controls were used, which were negative for all patients.

Using an anti-α7A polyclonal antibody, little or no fluorescence signal was detected in all SPMD patients, indicating a complete absence of α7A in the skeletal muscles of these patients (FIG. 12). In contrast, α7B integrin fluorescence was detected in muscle biopsy samples from patient #5 and #9 but not in #4 (FIG. 12).

The β1D integrin isoform is the heterodimeric partner of α7 integrin in skeletal and cardiac muscle. Because of the altered expression of the α7 integrin in these patients we examined if expression of the β1 integrin protein was also affected. FIG. 12 shows that β1D integrin immunofluorescence was comparable in the normal and SPMD biopsy materials. Accordingly, we conclude that β1D integrin expression is normal in this form of muscular dystrophy.

Because previous studies have shown that the α7 protein is absent from the muscles of laminin-2/4 (α2β1γ1)-deficient patients and dy mice, we examined whether there was a similar lack of laminin expression in the muscular biopsies from the SPMD patients. Our results showed that all the SPMD patients analyzed have laminin-2/4 in the matrix surrounding muscle fibers, indicating that the reduction or lack of α7 integrin is not secondary to the loss of laminin-2/4 (merosin).

Due to the absence of α7A integrin in the muscle of SPMD patients, we determined the localization and relative levels of expression of other muscle protein involved in the stability and integrity of muscle fibers. All five SPMD patients showed dystrophin expression. However, the levels of dystrophin appeared significantly higher than in normal control muscle biopsies.

Utrophin, a protein closely related to dystrophin, is normally restricted to neuromuscular junctions. In all SPMD patients utrophin immunofluorescence was not only found at neuromuscular junctions but also around muscle fibers, especially in patients #5 and #9. These results indicate that SPMD pathology results in a weakening of the matrix-muscle fiber interactions (as in DMD) and a compensatory change in the localization and expression of the utrophin protein to stabilize muscle fibers.

Neuromuscular junctions (detected by staining acetylcholine receptors (AchRs) with rhodamine labeled α-bungarotoxin) appeared smaller and fragmented in SPMD patients as compared to those of normal controls.

To determine the extent of pathology of SPMD patients analyzed in this study, hematoxylin and eosin (H&E) staining of 10 μm cryosections were carried out. Patient #4 had moderate variations in muscle fiber diameter, infiltration of mononuclear cells and centrally located nuclei. Patient #5 had less severe abnormalities, but gaps were evident between muscle fibers.

Figure 11:
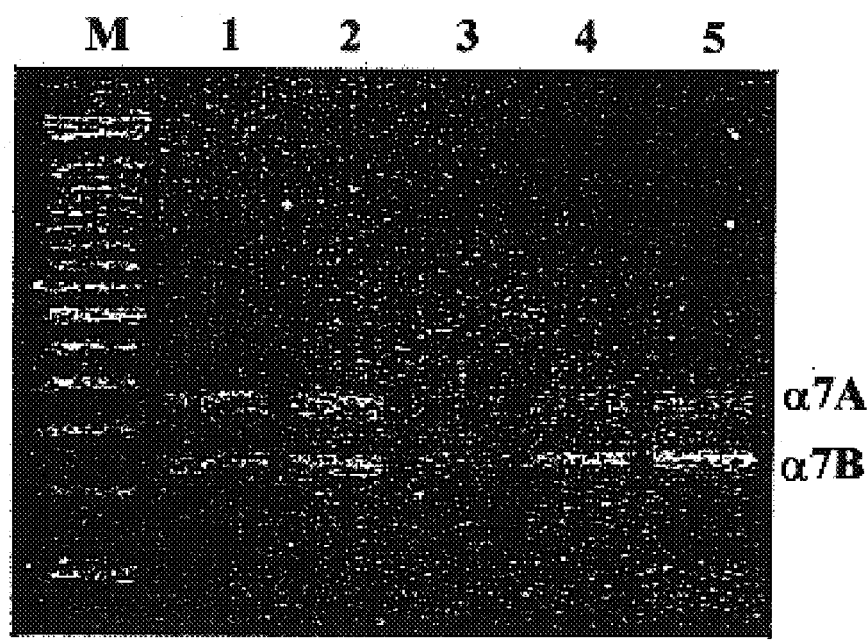
FIG. 11 documents PCR detection of integrin α7A and α7B in normal control and SPMD patient samples. 35 cycles of amplification reveal minimal amounts of α7A in the SPMD patient samples.

SPMD is diagnosed when the transcriptional or translational expression of the α7A integrin isoform is reduced in muscle tissue biopsy samples taken from a patient exhibiting muscular dystrophy symptoms. Detection of α7A integrin expression can be via immunological analysis, or it can be via α7A integrin specific hybridization probes or using α7A integrin-specific primers for use in a reverse transcriptase polymerase chain reaction assay with the detection of the α7A integrin amplification product of a specific size, as described herein below (FIG. 11). Using the particular primers described hereinbelow, the α7A amplification product is 451 bp whereas the amplification product produced from an α7B transcript is 338 bp in length. One of ordinary skill in the art can readily modify the primers specifically disclosed herein to arrive at functionally equivalent primers, i.e., those which provide for distinction by size (or sequence at the splice junction regions) of the integrin α7 transcript. Similarly, alternative monoclonal antibodies which distinguish the α7 polypeptides can be developed using art-known technology.

Monoclonal or polyclonal antibodies, preferably monoclonal, specifically reacting with a particular integrin subunit polypeptide or encoded by a particular coding sequence, especially an α7⊕1 integrin, have been made by methods known in the art. See, e.g., Harlow and Lane (1988) Antibodies: A Laboratory Manual, Cold Spring Harbor Laboratories, Goding (1986) Monoclonal Antibodies: Principles and Practice, 2d ed., Academic Press, New York; and Ausubel et al. (1993) Current Protocols in Molecular Biology, Wiley Interscience, New York, N.Y.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) Molecular Cloning, Second Edition, Cold Spring Harbor Laboratory, Plainview, N.Y.; Maniatis et al. (1982) Molecular Cloning, Cold Spring Harbor Laboratory, Plainview, N.Y.; Wu (ed.) (1993) Meth. Enzymol. 218, Part 1; Wu (ed) (1979) Meth. Enzymol. 68; Wu et al. (eds.) (1983) Meth. Enzymol. 100 and 101. Grossman and Moldave (eds.) Meth. Enzymol. 65; Miller (ed.) (1972) Experiments in Molecular Genetics, Cold Spring Harbor Laboratory, Cold Spring Harbor, N.Y., Old and Primrose (1981) Principles of Gene Manipulation, University of California Press, Berkeley; Schleif and Wensink (1982) Practical Methods in Molecular Biology; Glover (ed.) (1985) DNA Cloning Vol I and II, IRL Press, Oxford, UK; Hames and Higgins (eds.) (1985) Nucleic Acid Hybridization; IRL Press Oxford, UK; Setlow and Hollaender (1979) Genetic Engineering: Principles and Methods, Vols 1–4, Plenum Press, New York, and Ausubel et al. (1992) Current Protocols in Molecular Biology, Greene/Wiley, New York, N.Y. Abbreviations and nomenclature, where employed, are deemed standard in the field and commonly used in professional journals such as those cited herein.

All references cited in the present application are incorporated by reference herein to the extent that there is no inconsistency with the present disclosure.

The following examples are provided for illustrative purposes, and are not intended to limit the scope of the invention as claimed herein. Any variations in the exemplified articles which occur to the skilled artisan are intended to fall within the scope of the present invention.

EXAMPLES

Example 1

MCK-α7BX2 Integrin Construct

The cDNA encoding the rat α7BX2 integrin isoform was cloned into the pBK-RSV vector (Stratagene, La Jolla, Calif.) downstream of the 3.3 kb mouse muscle creatine kinase promoter (MCK, described in Jaynes et al., 1986) and the mouse α7 integrin cell surface localization signal sequence using the restriction sites AatII and KpnI. The MCK promoter was kindly provided by Dr. Stephen Hauschka, (University of Washington). The construct was verified by DNA sequencing. Previous studies have shown that the MCK promoter is only active in heart and skeletal muscle (Jaynes et al., 1986; Johnson et al., 1989; Shield et al., 1996). The expression and functionality of the MCK-α7BX2 integrin construct was verified by transfecting C2C12 myoblasts (Burkin et al., 1998; Burkin et al., 2000). The sequence of the integrin α7 subunit is given in Song et al. (1992) . See also Burkin and Kaufman (1998) for a discussion of the MCK-regulated construct.

Example 2

Production of Transgenic mdx/utr(−/−) Mice

The MCK-α7BX2 construct-containing DNA fragment was gel purified. F1 female mice from a C57BL6 X SJ6 strain cross were superovulated, mated to F1 male mice and fertilized oocytes were collected. The MCK-α7BX2 construct was microinjected into male pronuclei and injected oocytes were placed into pseudopregnant mice at the University of Illinois Transgenic Animal Facility. Resulting pups were weaned at 3 weeks of age. Genomic DNA was isolated from 0.5 cm tail clips using a DNA isolation kit (Promega, Madison, Wis.). Primers (MCK1: 5'-caagctgcacgcctgggtcc-3', SEQ ID NO:1; and AAT1l: 5'-ggcacccatgacgtccagattgaag-3'; SEQ ID NO:2) used to amplify between the MCK promoter and the α7 integrin cDNA resulted in a 455 bp amplimer only in transgenic mice. Transgenic male F1 mice were bred with mds/utr (+/−) female mice, provided by Dr. Joshua Sanes (Washington University, St. Louis, Mo.).

All male offspring were mdx due to the location of the dystrophin gene on the mouse X-chromosome. The mdx mutation was also screened by the amplification resistant mutation system described by Amalfitano and Chamberlain (1996). A new forward primer (Int22-306F. 5'-catagttattaatgcatagatattcag-3, SEQ ID NO:3), upstream of the mdx mutation site was used to yield a larger, 275 bp band. The status of the utrophin gene was analyzed by PCR using the primers 553, 554 and 22803 previously described by Grady et al., (1997a). Transgenic mdx/utr (+/−) males were bred with mdx/utr (+/−) female mice to produce transgenic α7BX2 mdx/utr (−/−) mice.

Example 3

Tissue Collection and Storage

Muscle biopsies were obtained from SPMD or other dystrophic patients and from normal humans using local anaesthetic. All patients were from the same family and showed varying degrees of SPMD pathology. Muscle tissue from the right vastus lateralis muscle were obtained from Patients #4 and 5. Patients #6–9 provided muscle tissue from the left vastus lateralis muscle. Irrelevant biopsy samples from the same patients served as controls. Biopsied muscle samples were frozen in liquid nitrogen immediately after removal. Further control muscle samples were obtained from normal individuals without any known muscle diseases. Muscle samples were stored at −80° C. prior to analysis.

Example 4

Antibodies and Reagents

For western blot analysis, the polyclonal antibody specific for α7CDA(345) and polyclonal antibody specific for α7CDB(347) were used to detect the α7A and α7B integrin cytoplasmic domains, respectively (Song et al., 1993): Peptides used to make these polyclonal antibodies were used as blocking controls. The monoclonal antibody O5 was used as a pan-α7 integrin probe. For immunofluorescence analysis the pan-α7 integrin monoclonal antibody O26 was used to detect all α7 integrin chains. Rabbit polyclonal antibodies to the cytoplasmic domains of the α7A and β1D integrin chains were provided by Dr. W. K. Song (See Kim et al, 1999, Cell Adhes. Commun 7:85–87). Dystrophin was detected using an anti-dystrophin monoclonal antibody (MANDRA1) purchased from Sigma Chemical Co., St. Louis, Mo. Culture fluid from the anti-utrophin monoclonal antibody-producing hybridoma (NCL-DRP2) was purchased from Novacastra Laboratories, Ltd. The anti-fetal myosin heavy light chain (fMYHC) monoclonal antibody 47A was obtained from Dr. Peter Merrifield (University of Western Ontario). AChR clusters were detected using rhodamine-labeled α-bungarotoxin purchased from Molecular Probes, Eugene, Oreg. FITC-labeled donkey anti-mouse and anti-rabbit antibodies were purchased from Jackson Laboratories, Bar Harbor, Me. The anti-creatine kinase monoclonal antibody (anti-CKIM) was obtained from AD1 Diagnostics, Rexdale, Ontario.

Example 5

Western Analysis

Samples of muscle tissue were extracted in 200 mM octyl-β-D-glucopyranoside, 50 mM Tris HCl, pH 7.4, 2 mM phenylmethylsulfonyl fluoride, 1 200 dilution of Protease Cocktail Set III (Calbiochem, San Diego, Calif.) 1 mM $CaCl_2$, 1 mM $MgCl_2$ at 4° C. for 1 hr. Particulate material was removed by centrifugation, and the supernatants were collected. Protein concentrations were determined according to Bradford, M. (1976) Anal. Biochem. 72:248–254. Equal amounts of extracted muscle proteins were separated by sodium dodecyl sulfate polyacrylamide (8%) gel electrophoresis at 40 mA for 50 min. The proteins were transferred to nitrocellulose filters. Filters were blocked using 10% horse serum in PCS, and the blocked filters were incubated with a 1:500 dilution of polyclonal anti-α7CDA(345) and anti-α7CDB(347) primary antibodies that recognize the A and B cytoplasmic domains, respectively (Song et al., 1993). Horseradish peroxidase (HRP)-linked anti-rabbit secondary antibody was used to detect bound primary antibody. Immunoreactive protein bands were detected using an Enhanced Chemiluminescence kit (Amersham, Arlington Heights, Ill.). Specificity of the bands was confirmed using the blocking peptides which served as immunogens in the production of the A2 (anti-α7A) and B2 (anti-α7B) antibody preparations. Blots were re-probed with an anti-creatine kinase antibody. The intensities of the α7 bands were compared to creatine kinase using ImageQuant software (Molecular Dynamics, Sunnyvale, Calif.).

Example 6

Immunofluorescence Analyses

Quadriceps muscles from 10 week old male mdx, mdx/utr (−/−) an α7BX2-mdx/utr (−/−) were embedded in OCT (polyvinyl alcohol and polyethylene glycol) compound (Tissue-Tek, Torrance, Calif.) and frozen in liquid nitrogen cooled isopentane. Using a Leica CM 1900 series cryostat, 10 μm sections were cut and placed on microscope slides coated with 1% gelatin, 0.05% chromium potassium sulfate. Sections were fixed in −20° C. acetone for 1 min, rehydrated in phosphate buffered saline (PBS) for 10 mm and blocked in PBS containing 10% horse serum for 15 min. The rat α7 chain was detected using 5 μg/ml of purified O26 monoclonal antibody directly labeled with Alexa 488 (Molecular Probes, Eugene, Oreg.). The anti-β1D antibody was used at a 1:100 dilution in 1% horse serum in PBS. The anti-dystrophin antibody was used at a 1:100 dilution while anti-utrophin and anti-fMyHC antibodies were diluted 1:2 in 1% horse serum, PBS. Rhodamine labeled α-bungarotoxin was used at a 1:3000 dilution to detect neuromuscular junctions.

Endogenous mouse immunoglobulin was blocked before the addition of monoclonal antibodies using 60 µg/ml goat anti-mouse monovalent Fabs (Jackson Laboratories,) in 1% horse serum in PBS, for 30 min at room temperature. Slides were then washed three times for 5 min each time in 1% horse serum in PBS. Primary antibodies were added for 1 hour at room temperature. Slides were washed 3 times (5 min per wash) in 1% horse serum. PBS Primary antibodies were detected with a 1:100 dilution of FITC-labeled donkey antimouse or anti-rabbit antibody in 1% horse serum in PBS. Slides were mounted using Vectorshield mountant (Vector Labs, Burlingame, Calif.). Localization of the antibody was observed with a Zeiss Photomicroscope III (Carl Zeiss, Inc., Thornwood, N.Y.). Images of were acquired with a Sony DXC9000 color video CCD camera using SiteCam software (Sony, Tokyo, Japan).

Muscle biopsies from normal individuals and SPMD patients were embedded in OCT compound and frozen in liquid nitrogen cooled isopentane. Using a Leica CM1900 series cryostat, 10 µm sections were placed on microscope slides coated with 1% gelatin, 0.05% chromium potassium sulfate. Sections were fixed in ice cold acetone for 1 min. rehydrated in phosphate buffered saline (PBS) for 10 min and blocked in PBS containing 10% horse serum for 15 min. The α7 integrin protein was detected using 35 µg/ml purified O26 monoclonal antibody in 1% horse serum, 1×PBS. The anti-b1D antibody was used at a 1:100 dilution in 1% horse serum, 1×PBS. The anti-dystrophin antibody was used at a 1:100 dilution and anti-utrophin and anti-merosin antibodies were diluted 1:2 in 1% horse serum in 1×PBS. Rhodamine-labeled bungarotoxin was used at a 1:1000 dilution to detect neuromuscular junctions. After the addition of primary antibody, slides were incubated for 1 hr at room temperature in a humidified chamber. Slides were washed 3 times (5 min each) in 1% horse serum, 1×PBS. Primary monoclonal antibodies were detected using a 1:1000 dilution of FITC-labeled donkey anti-mouse or anti-rabbit antibody in 1% horse serum, 1×PBS. Washed slides were mounted in Vectorshield mountant (Vector Laboratories, Burlingame, Calif.) and coverslipped. Human α7 integrin protein bands were visualized using a Zeiss Photomicroscope III (Carl Zeiss, Inc., Thornwood, N.Y.). Images were acquired using a Sony DXC9000 color video CCD camera and Sitecam software.

Example 7

Histology

Ten micron cryosections from the quadriceps muscles of 5, 8 and 10 week old wildtype, mdx, mdx/utr (−/−) and transgenic mdx/utr (−/−) mice were placed on uncoated slides and stained with hematoxylin and eosin. The occurrence of central nuclei was scored in a minimum of 1000 fibers in two mice from each line.

Example 8

X-ray and Magnetic Resonance Imaging

Spinal curvature (kyphosis) in 10 week old mdx, mdx/utr (−/−) and transgenic α7BX2 mdx/utr (−/−) mice was visualize by X-ray imaging using a Siemens Hehodent 70 X-ray machine (model D3104). X-rays were taken at 70 kVp and 7 mA.

Magnetic resonance imaging (MRI) of 10 week old wildtype, mdx, mdx/utr (−/−) and α7BX2-mdx/utr (−/−) mice was used to visualize soft tissues. Mice were imaged at 1 mm thickness using a 4.7T/3lcm Surrey Medical Imaging Spectrophotometer.

Example 9

RT-PCR and Genomic DNA Analyses

Total RNA was extracted from frozen muscle biopsies using TRIzol reagent (monophasic solution of phenol and guanidine isothiocyanate. U.S. Pat. No. 5,346,994, Gibco-BRL Gaithersburg, Md.). A panel of overlapping primers designed from the α7 cDNA sequence were used in RT-PCR reactions to screen patient RNA for transcriptional expression of the integrin α7A subunit isoform.

The primers used to amplify around the human α7Aα7B alternative splice site are hu3101F 5'-GAACAGCACCTTTCTGAGG-3' (SEQ ID NO:4) and hu3438R 5'-CCTTGAACTGCTGTCGGTCT-3' (SEQ ID NO:5). In SPMD patients there is very little α7A amplification product in comparison to the amount seen in a normal individual. The expected product sizes from the use of these primers in a polymerase chain reaction are for α7A: 451 bp band; α7B: 338 bp band. The numbers in the primer names correspond to the location in the human cDNA sequence, F denotes a forward primer and R denotes a reverse primer.

For Southern hybridization analyses, mouse genomic DNA was isolated from whole blood or liver using a genomic DNA isolation kit (Promega). DNA was cleaved with EcoRI and KpnI at 3 U/µg of DNA for 16 hours. DNA fragments were separated on 0.8% agarose gels and alkaline transferred to Hybond-XL nylon membranes (Amersham) (Sambrook et al., 1989). A 367 bp probe from the rat α7 3'-non-translated domain was isolated. The probe was directly labeled with HRP using a North2South non-radioactive kit (Pierce Scientific, Rockford, Ill.). The hybridized blots were washed following manufacturer's instructions. Probes were detected using an ECL substrate (luminol and $H_2O_2$, Amersham Life Science, Arlington Heights, Ill.). Blots were exposed to X-ray film from 1 to 30 min.

Example 10

Reporter Construction

TABLE 1

DNA sequence and Restriction Map of a7 Integrin Promoter Region (1970bp) (SEQ ID NO:6)

GAAAGTAGAATCCTGGTGCCAGCCCTGCTGACAGCATATGTATTTCCTTATAGTACCTGTTTAGA

GATGTGTTAGTGCTCTGGAGGGATAGCCACAGGTGTAGTATTGGAAAACAGAGGGCCAGACT

TABLE 1-continued

DNA sequence and Restriction Map of a7 Integrin Promoter Region (1970bp) (SEQ ID NO.6)

TCCAAATGTCTGTTAACTTATCCAAGGCAAAGACTGTCCCAGGGCAGCAGAGTAAGAACCCACT

TTTTTTTTGTTTTCAAAGAAGTATAATCCTGAACAATGAAGTAGGAAAGACAGAACACAGGAAGA

GGAAGGAGGTAGGACACTTATTGGAATTTTAAGAAAGGGAAAGAGAAGAAAGAATCGTAAGAA

TATGATAGTGTTTGAAGGGCAGAGACAACACTAGAAACATTGAGAAATACTCTGAGAAAGATTCC

AAGTGTGGCAGAGACAAGAATGATGACAAAATAGAATTTGGGATGAGACAAAATCAGATAGTGA

GAGAGAGAAGGGAAGATGGACAGATGTATATTCACAAGACCAACACCAGTAAGCAAGGGGACT

AGGAAGGGGAAGTGGGAGCATTCGAGGTTCCCATTATGCCAAATTATTTCCTGTCTCTCCTTCT

GGCCCCATTTCTGTATCGGAGTTATAAATAGCAGAGAGTTGGAAAGTGTCCCCCCACCCCCTTG

CCTCTGTCCCAGCCTGAGGGAAAGGGAGAGGAAGAGGGACAGGCCAATGGGTCCCTGTGGAG

ATCCCATCTCAGCCCCACCCAGGTCCTGCTGAGCCAGTCCAGGACTCTGCCCCCTCCCATCCC

CTTTCATGGATAGGAAATGTGCAGTCCTGGGACGGGTCTGGTAGCTGGGGACACCCTTTACAT

CCCTCTGCCTCTTGGGTCCAGTCTCTTTCATCTTTGCCTTCTTTGACACCCACTCCCCTCCCCAC

TGCTTAATTTCCTCTTCCTGTAATCATCCCCAGTCGTTTTCTTTTCTCCCTTCATTCCATCCCTTGT

CAATTAATCTCTTGCCCTTCTTTCTTCCTCTCTATTCCTTTCCTTTTTCCATTTCTCCATTTGCTCC

CCGTATCTCCCGAGTTTCTCTCTCTCTTCTTGCCTCTTTTTCTCTGTTCCCTTGAATCCTGACGAT

GTGGCTAGCACTGCTGTGGTCATTGCCGGGCTGGGGCGGGGGATGGGATAGGATGGGGGA

GGGCAGCGGTCTGATCCCAACAGCAGAAAGAGTGCTCTATGTGACCATGGGGGAACAGGGAG

CACTAAGATGCCACGCTGCACCCAGGCCCAGGACGGCTCCCCTTTCATTTCCTCTCTATCTGCA

CATCTCTCTTCCCAGGTTGTCTTTTAGCGTCTTCCCAACTTCTCATCTCTTACCCTCCTTCCTCTG

TTTCAGCCCCTCTCTTTCTATCTGTACTTCTCTCCCTCCGCATTCCAAGGCGCCGCCTCCACCAC

TCCCGGGGTGGGGATGGGGTTGGGGGAGAAGGGGAGGAGAGCGCCGCGCAGGGCGGAGC

CGGAGACGGTGCTGGGCTTGGGGGGCGTGGTGGTGGGGGGTCAGCAAGGCTAGTTTCCATC

CCAGCCACCAGCCTGGGCATCCCCTTGGAGACGGGCTTGGGTCTCCACCTGCCGCGGGAGCG

AGGGGCGGGGCCGGAGGCGGGGCCTGAGTGGCGTCCCCGGGAGAGGAGGCGGGAGCCGG

AGTGGGCGCCGGAGCTGCGGCTGCTGTAGTTGTCCTAGCCGGTGCTGGGGCGGCGGGGTGG

CGGAGCGGCGGGCGGGCGGGAGGGCTGGCGGGGCGAACGTCTGGGAGACGTCTGAAAGAC

CAACGAGACTTTGGAGACCAGAGACGCGCCTGGGGGGACCTGGGGCTTGGGGCGTGCGAGA

TTTCCCTTGCATTCGCTGGGAGCTCGCGCAGGGATCGTCCC<u>ATG</u>GCCGGGGCTCGGAGCCGC

GACCCTTGGGGGGCCTCCGGGATTTGCTACCTTTTTGGCTCCCTGCTCGTCGAACTGCTCTTCT

CACGGGCT

Underlined: Translational start site.

A luciferase reporter system is used to analyze promoter activity and to identify compounds which modulate (increase or decrease) promoter activity. The isolated α7 integrin promoter sequences are subcloned into the pA3Luc vector so that the firefly luciferase gene is under the transcriptional control of the human α7 promoter. These constructs are transfected into a human myoblast cell line along with a control vector phRL-TK(lnt-) containing the Renilla luciferase gene coding sequence. Cotransfection with the Renilla construct is used to control transfection efficiency. The different fragments of the humna α7 gene are analyzed to determine which contains the greatest activity as determined by the luciferase reporter. The fragment with maximum activity is subcloned into the β-lactamase reporter system for subsequent screens. In addition to the approximately 2 kb transcriptional regulation sequences disclosed herein. an approximately 5 kb fragment of the human α7 integrin promoter is also useful in reporter gene constructs. Another reporter system useful in the context of the present is the GeneBLAzer β-lactamase reporter technology (Aurora Biosciences Corporation, San Diego, Calif.).

The reporter gene constructs of the present invention are transformed into myoblasts or myotendinous cells. These cells in which the reporter gene vector is maintained are contacted with test compounds, and the effect on reporter gene expression is monitored (fluorescence intensity where the reporter gene coding sequence is that of a fluorescent protein such as aequorin) and by measurement of a detectable product of an enzyme coding sequence, e.g. and enzyme activity such as that of β-lactamase in the case of the GeneBLAzer system or that of luciferase using the reporter vector described above. Those compounds which cause a higher level of reporter activity in the presence of the presence than in the absence of the compound are those which stimulate expression of the intact α7 integrin. These compounds similarly increase the level of α7 integrin in muscle and myotendinous cells. As demonstrated herein, increased expression leads to an amelioration of the muscular dystrophy symptoms.

The human α7 integrin transcription regulatory sequences are identified as part of the Homo sapiens chromosome 12 BAC, RP11-6445F BAC nucleotide sequence is available under GenBank Accession No. AC009779, deposited by K. C. Worley.

Example 11

Statistical Analysis

Survival data from 84 mdx/utr (−/−) mice and 43 transgenic α7BX2-mdx/utr (−/−) mice were analyzed using the Kaplan-Meier method (Kaplan and Meier, 1958). Survival curves were generated for both populations and the data compared using log-rank (Peto et al., 1977) and Wilcoxon (Conover et al., 1980) statistical tests

TABLE 2

| | Percent fibers with central nuclei | | |
|---|---|---|---|
| | 5 weeks | 8 weeks | 10 weeks |
| Wt | 2.6 | 1.3 | 2.7 |
| Mdx | 33.0 | 65.6 | 70.9 |
| mdx/utr (−/−) | 79.0 | 78.4 | 75.2 |
| a7BX2-mdx/utr (−/−) | 62.1 | 71.7 | 63.9 |

Sections of hindlimb muscle from 5.8, and 10 week old mice were stained with hematoxylin and eosin. Nuclear localization was scored in at least 1000 fibers in each animal.

References Cited in the Present Application

Amalfitano, A. and J. S. Chamberlain. 1996. The mdx-amplification-resistant mutation system assay, a simple and rapid polymerase chain reaction-based detection of the mdx allele. Muscle Nerve 19: 1549–1553.

Ascadi et al. 1996. Dystrophin expression in muscles of mdx mice after adenovirus-mediated in vivo gene transfer. Hum. Gene Ther. 7: 129–140.

Belkin, A. M. et al. 1996. Beta 1D integrin displaces the beta 1A isoform in striated muscles localization at junctional structures and signaling potential in nonmuscle cells. J. Cell Biol. 132:211–216.

Belkin, A. M. et al. 1997. Muscle beta1D integrin reinforces the cytoskeleton-matrix link: modulation of integrin adhesive function by alternative splicing J. Cell Biol. 139:1583–1595.

Bertorini, T. E., et al 1986. Muscle calcium and magnesium content in Duchenne muscular dystrophy. Neurology 32: 1088–1092.

Bradford, M. 1976. Anal. Biochem. 72: 248–254.

Bulfield, O. Et al. 1984. X chromosome-linked muscular dystrophy (mdx) in the mouse. Proc Natl. Acad. Sci USA 81: 1189–1192.

Burkin, D. J. et al. 1998. A functional role for specific spliced variants of the α7β1 integrin in acetylcholine receptor clustering. J. Cell Biol. 143: 1067–1075.

Burkin D. J. and S. J. Kaufman. 1999. The α7β1 integrin in muscle development and disease. Cell Tiss. Res. 296: 183–190.

Burkin, D. J. et al. 2000. Laminin and α7β1 integrin regulate agrin-induced clustering of acetylcholine receptors. J. Cell Sci. 113: 2877–2886.

Campbell, K. P. 1995. Three muscular dystrophies: loss of cytoskeleton-extracellular matrix linkage. Cell 80: 675–679.

Campeau, P. et al. 2001. Transfection of large plasmids in primary human myoblasts. Gene Therapy 8: 1387–1394.

Collo, G. et al. 1993. A new isoform of the laminin receptor integrin alpha 7 beta 1 is developmentally regulated in skeletal muscle. J. Biol. Chem. 268: 19019–19024.

Colognato, H. et al. 1999. Laminin polymerization induces a receptor-cytoskeleton network. J. Cell Biol. 145: 619–631.

Conover, W. J. 1980. Practical Nonparametric Statistics, 2nd ed., John Wiley & Sons, New York, Cordier et al. 200. Mol. Ther. 1: 119–129.

Deconinck, A. E. et al. 1997a. Postsynaptic abnormalities at the neuromuscular junctions of utrophin-deficient mice. J. Cell Biol. 136: 883–894.

Deconinck, A. E. et al. 1997b. Utrophin-dystrophin deficient mice as a model for Duchenne muscular dystrophy. Cell 90: 717–727.

Denetclaw, W. F. Jr. et al. 1994. Myotubes from transgenic mdx mice expressing full-length dystrophin show normal calcium regulation. Mol. Biol. Cell. 5:1159–1167.

DiMario, J. X. et al. 1991. Fiber regeneration is not persistent in dystrophic (mdx) mouse skeletal muscle. Dev. Biol. 148: 314–321.

Donoviel, D. B. et al 1996 Analysis of muscle creatine kinase gene regulatory elements in skeletal and cardiac muscles of transgenic mice. Mol. Cell. Biol. 16: 1649–1658.

Ebihara et al. 2000. Differential effects of dystrophin and utrophin gene transfer in immunocompetent muscular dystrophy (mdx) mice. Physiol. Genomics 3: 133–144.

Fujii et al 2000. Targeted and stable gene delivery into muscle cells by a two-step transfer. Biochem. Biophys. Res. Commun. 275: 931–935

Gilbert et al. 1999. Efficient utrophin exzpression following adenovirus gene transfer in dystrophic muscles. Biochem. Biophys. Res. Commun. 242: 2440247.

Grady, R. M. et al 1997a Subtle neuromuscular defects in utrophin deficient mice. J. Cell Biol. 136: 871–882.

Grady, R. M. et al. 1997b. Skeletal and cardiac myopathies in mice lacking utrophin and dystrophin: a model for Duchenne muscular dystrophy. Cell 90: 72–738.

Grady, R. M. et al. 1999. Role for alpha-dystrobrevin in the pathogenesis of dystrophin-dependent muscular dystrophies. Nat. Cell Biol. 1: 215–220.

Greelish et al. 1999. Nat. Med. 5: 4439–443. Xiao et al. (2000), Cordier et al. (2000).

Hayashi, Y. K. et al. 1993. Abnormal localization of laminin subunits in muscular dystrophies. J. Neurol. Sci. 119: 53–64.

Hayashi, Y. K. et al. 1998. Mutations in the integrin α7 gene cause congenital myopathy. Nat. Gen. 19: 94–97.

Hodges, B. L. and S. J. Kaufman. 1996. Developmental regulation and functional significance of alternative splicing of NCAM and α7β1 integrin in skeletal muscle. Basic Appl. Myology 6: 437–446.

Hodges, B. L. et al. 1997. Altered expression of the α7β1 integrin in human and murine muscular dystrophies. J. Cell. Sci. 110: 2873–2881.

Hynes, R. O. 1992. Integrins: versatility, modulation, and signaling in cell adhesion. Cell 69:11–25

Jaynes, J. B. et al. 1986. Transcriptional regulation of the muscle creatine kinase gene and related expression in transfected mouse myoblasts. Mol. Cell. Biol. 6: 2855–2864.

Johnson, J. F. et al. 1989. Muscle creatine kinase sequence elements regulating skeletal and cardiac muscle expression in transgenic mice. Mol. Cell Biol. 9: 3393–3399.

Kaplan, E. L. and P. Meier. 1958. Nonparametric estimation from incomplete observations. J. Am. Stat. Assoc. 53: 457–481.

Kim, Y. Y. et al. 1999. Cellular localization of α3β1 integrin isoforms in association with myofibrillogenesis during cardiac myocyte development in culture Cell Adhesion and Comm. 7: 85–97.

Kwon, M. S. et al. 2000. Calreticulin couples calcium release and calcium influx in α7β1 integrin-mediated calcium signaling Mol. Cell Biol. 11: 1433–1443.

Law, D. J. et al. 1994. Talin, vinculin and DRP (utrophin) concentrations are increased at the mdx myotendinous junctions following onset of necrosis. J. Cell Sci. 107: 1477–1483.

Leung, E. et al. 1998. A novel extracellular domain variant of the human integrin α7 subunit generated by alternative intron splicing. Biochem. Biophys. Res. Commun. 243: 317–325.

Lim, L. E. and K. P. Campbell. 1998. The sarcoglycan complex in limb-girdle muscular dystropy. Curr. Opin. Neurol. 11: 443–452.

Martin, P. T. et al. 1996. Synaptic integrins: selective association of the α1 and α7A, and α7B subunits with the neuromuscular junction. Dev. Biol. 174: 125–139.

Matsuda, R. et al. 1983. Regenerating adult chicken skeletal muscle and satellite cells cultures express embryonic patterns of myosin and tropomyosin isoforms. Dev. Biol. 100: 478–488.

Matsumura, K. et al. 1992. Association of dystrophin-related protein with dystrophin-associated proteins in mdx mouse muscle. Nature 360: 588–591.

Matsumura, K. and K. P. Campbell. 1994. Dystrophin-glycoprotein complex: its role in the molecular pathogenesis of muscular dystrophies. Muscle Nerve 17: 2–15.

Mayer, U. et al. 1997. Absence of integrin alpha 7 causes a novel form of muscular dystrophy. Nat. Genet. 17: 318–323.

Monaco, A. P. et al. 1986. Isolation of candidate cDNAs for portions of the Duchenne muscular dystrophy gene. Nature. 323: 646–650.

Muzyczka, N. 1992. Curr. Top. Microbiol. Immunol. 158: 97–129.

Oda, T. et al. 1993. Longitudinal study of spinal deformity in Duchenne muscular dystrophy J. Pediatr. Orthop. 13:478–488.

Peto, R. et al. 1977. Design and analysis of randomized clinical trials requiring prolonged observation of each patient. II. Analysis and examples. Brit. J. Cancer 35: 1–39.

Poirier et al. 2000. Increased intracellular triglyceride in C(2)C(12) msucle cells transfercted with a human lipoprotein lipase. Biochem. Biophys. Res. Commun. 270: 997–1001.

Pons, F. et al. 1994. Does utrophin expression in muscles of mdx mice during postnatal development functionally compensate for dystrophin deficiency. J. Neurol. Sci. 122: 162–170.

Rafael, J. A. et al. 1998. Skeletal muscle-specific expression of a utrophin transgenic rescues utrophin-dystrophin deficient mice. Nat. Gen. 19: 79–82.

Rafael, J. A. et al. 2000. Dystrophin and utrophin influence fiber type composition and post-synaptic membrane structure. Hum. Mol. Gene: 9 1357–1367.

Ragot et al. (1993) Nature 361: 647.

Sand, A. D. et al. 1987. Immunochemical analysis of protein isoforms in thick myofilaments of regenerating skeletal muscle. Dev. Biol. 119: 336–349.

Saher, G. and E. Hildt. 1999 Activation of c-Raf-1 kinase signal transduction pathway in alpha(7) integrin-deficient mice. J. Biol. Chem. 274: 27651–27657.

Shield, M. A et al. 1996. E-box sites and a proximal regulatory region of the muscle creatine kinase gene differentially regulate expression in diverse skeletal muscles and cardiac muscle of transgenic mice. Mol. Cell. Biol. 16: 5058–5068.

Sicinski, P. et al. 1989. The molecular basis of muscular dystrophy in the mdx mouse. A point mutation. Science 244: 1578–1580.

Song W. K. et al. 1992. H36-α7 is a novel integrin alpha chain that is developmentally regulated during skeletal myogenesis. J. Cell Biol. 117: 643–667.

Song, W. K. et al. 1993. Expression of α7 integrin cytoplasmic domains during skeletal muscle development: alternate forms, conformational change, and homologieswith serine/threonine kinases and tyrosine phosphatases. J. Cell Sci. 106: 1139–1152

Stedman, H. 2001. Molecular approaches to therapy for Duchenne and limb girdle muscular dystrophy. Curr. Opin. Molec. Therap. 3: 350–356.

Tinsley, J. M. et al. 1996. Amelioration of the dystrophin phenotype of mdx mice using a truncated utrophin transgene. Nature 384: 349–353.

Turner, P. R. et al. 1988. Increased protein degradation results from elevated free calcium levels found in muscle from mdx mice. Nature 335: 735–738.

Vignier, N. et al. 1999. Structure, genetic localization, and identification of the cardiac and skeletal muscle transcripts of the human integrin alpha 7 gene (ITGA). Biochem. Biophys. Res. Commun. 260: 357–364.

van der Flier, A. et al. 1995. A novel beta 1 integrin isoform produced by alternative splicing: unique expression in cardiac and skeletal muscle. FEBS Lett. 369: 340–344.

von der Mark, H. J. et al. 1991. Skeletal myoblasts utilize a novel α1-series integrin and not α6β1 for binding to the E8 and T8 fragments of laminin. J. Biol. Chem. 266: 23593–23601.

Wang, W. et al. 1995. Localization of the α7 integrin gene (ITGA7) on human chromosome 12q13. Clustering of integrin and hox genes implies parallel evolution of these gene families. Genomics 26: 563–570.

Wang, W. et al. 2000. Adeno-associated virus vector carrying human minidystrophin genes effectively ameliorates muscular dystrophy in mdx mouse model. Proc. Natl. Acad. Sci. USA 97: 13714–13719.

Xiao et al. 2000. J. Virol. 72. 10222–10226.

Yoon and Lee. 2000. Nature 408: 483–488.

Zhidkova, N. J. et al. 1995. Novel isoform of beta 1 integrin expressed in skeletal and cardiac muscle. Biochem. Biophys. Res. Commun. 214: 279–285.

Ziober B. L. et al. 1993. Alternative extracellular and cytoplasmic domains of the integrin α7 subunit are differentially expressed during development. J. Biol. Chem. 268: 26773–26783.

What is claimed is:

1. A method for identifying an individual exhibiting symptoms of a muscular dystrophy as an individual suffering from scapuloperoneal muscular dystrophy, said method comprising the steps of:

(a) obtaining a muscle tissue sample from an individual exhibiting symptoms of a dystrophy, wherein said individual is at least teen-aged and wherein said symptoms affecting the muscles of the shoulder girdle and peroneal, wherein said tissue sample is obtained from a tissue known in a normal individual to express α7A integrin;

(b) detecting a transcription product of an α7A integrin gene using hybridization or reverse transcriptase-polymerase chain reaction or a translation product of an α7A integrin gene using a detectable antibody specific for α7A integrin in said tissue sample;

(c) determining a level of the transcription or translation product of the α7A integrin gene in said tissue sample as compared with a level of the transcription or translation product of the integrin gene in a tissue sample from the same tissue of a normal individual;

(d) diagnosing scapuloperoneal muscular dystrophy when the tissue sample of an individual exhibiting muscular dystrophy symptoms comprises a level of a transcription or translation product of the α7A integrin gene in said tissue sample which is lower than the level in a tissue sample from the same tissue of a normal individual.

2. The method of claim 1 wherein the translation product of an α7A integrin gene in said tissue sample is detected by contacting the tissue sample using α7A integrin-specific antibody.

3. The method of claim 2 wherein the α7A integrin-specific antibody is detectably labeled.

* * * * *

UNITED STATES PATENT AND TRADEMARK OFFICE
CERTIFICATE OF CORRECTION

PATENT NO.    : 6,858,395 B2
DATED         : February 22, 2005
INVENTOR(S)   : Kaufman It is certified that error appears in the above-identified patent and that said Letters Patent is hereby corrected as shown below:

<u>Title page, Item [54] and Column 1, line 1,</u>
Title, insert a comma -- , -- between "DIAGNOSTICS" and "ASSAY";

<u>Title page,</u>
Item [56], References Cited, OTHER PUBLICATIONS,
"Monaco, A.P. et al.," reference, delete "1996" and replace with -- 1986 --.

<u>Column 2,</u>
Line 50, insert a period -- . -- between "splicing" and "β1A".
Line 59, delete "myopathics" and replace with -- myopathies --.

<u>Column 3,</u>
Line 55, delete "2 3-fold" and replace with -- 2.3-fold --.

<u>Column 4,</u>
Line 5, delete "through need," and replace with -- though needed, --.

<u>Column 7,</u>
Line 22, delete "(mcW+1 and mouse +is mdx." and replace with -- (mcW+) and mouse 4 is *mdx*. --.

<u>Column 8,</u>
Line 55, delete "reasonable" and replace with -- responsible --.

<u>Column 9,</u>
Line 20, delete "transfenic" and replace with -- transgenic --.
Line 40, delete "ATTH" and replace with -- AATII --.

<u>Column 10,</u>
Line 9, delete "stranger" and replace with -- stronger --.
Line 13, delete "contained" and replace with -- compared --.

<u>Column 11,</u>
Line 6, delete "stablizers" and replace with -- stabilizes --.
Line 15, delete "cosin" and replace with -- eosin --.

<u>Column 13,</u>
Line 17, delete "Similarity," and replace with -- Similarly --.
Line 24, delete "invention" and replace with -- inventor --.

UNITED STATES PATENT AND TRADEMARK OFFICE
CERTIFICATE OF CORRECTION

PATENT NO. : 6,858,395 B2
DATED : February 22, 2005
INVENTOR(S) : Kaufman

It is certified that error appears in the above-identified patent and that said Letters Patent is hereby corrected as shown below:

Column 14,
Line 14, delete "myvotendinous" and replace with -- myotendinous --.
Lines 26-27, delete "contributors" and replace with -- contributes --.
Line 61, delete "($[Ca^{2-}]i$)" and replace with -- ($[Ca^{2+}]i$) --.
Line 65, delete "$Ca^{2-}$-" and replace with -- $Ca^{2+}$- --.
Line 66, delete "$[Ca^{2-}]i$" and replace with -- $[Ca^{2+}]i$ --.

Column 15,
Line 4, delete "$[Ca^{2-}-]i$" and replace with -- $[Ca^{2+}-]i$ --.
Line 5, "$Ca^{2-}$-" and replace with -- $Ca^{2+}$- --.
Line 8, delete "charges" and replace with -- changes --.
Line 16, delete "C-Raf-1)/mitogen-activated" and replace with -- c-Raf-1/mitogen-activated --.

Column 16,
Line 1, insert a colon -- : -- between "assays" and "radioactive".

Column 17,
Lines 10 and 17, delete "α7B" and replace with -- α7β --.

Column 18,
Line 20, delete "α7⊕1" and replace with -- α7β1 --.

Column 20,
Line 30, delete "1    200" and replace with -- 1:200 --.

Column 22,
Line 30, delete "α7Aα7B" and replace with -- α7A/α7B --.
Line 32, delete "5'-GAACAGCACCTTTCTGAGG-3' " and replace with -- 5'-GAACAGCACCTTTCTGGAGG-3' --.
Header of Table 1, delete "Map of a7 Integrin Promoter" and replace with -- Map of α7 Integrin Promoter --.

UNITED STATES PATENT AND TRADEMARK OFFICE
CERTIFICATE OF CORRECTION

PATENT NO. : 6,858,395 B2
DATED : February 22, 2005
INVENTOR(S) : Kaufman

It is certified that error appears in the above-identified patent and that said Letters Patent is hereby corrected as shown below:

Column 23,
Line 3 of DNA sequence, delete
"GGAAGGAGGTAGGACACTTATTGGAATTTTAAGAAAGGGAAAGAGAAGAAAGAATCGTAAGAA" and replace with
-- GGAAGGAGGTAGGACACTTATTGGAACTTTTAAGAAAGGGAAAGAGAAGAAAGAATCGTAAGAA --.
Line 6 of DNA sequence, delete
"GAGAGAGAAGGGAAGATGGACAGATGTATATTCACAAGACCAACACCAGTAAGCAAGGGGACT" and replace with
-- GAGAGAGAAGGGAAGATGGACAGATGTATATTCACAAGACCAACACCAGTAAGCAAGGGGAGT --.

Column 24,
Line 60, delete "herein. an" and replace with -- herein, an --.

Column 25,
Line 18, delete "RP11-6445F BAC" and replace with -- RP11-6445F. This BAC --.
Line 41, delete "from 5.8, and 10 week old" and replace with -- from 5, 8, and 10 week old --.

Column 32,
Lines 56-58, in step (b), delete "a transcription product of an α7A integrin gene using hybridization or reverse transcriptase polymerase chain reaction or".
Lines 61 and 63, in step (c), delete "transcription or" before "translation".

UNITED STATES PATENT AND TRADEMARK OFFICE
CERTIFICATE OF CORRECTION

PATENT NO. : 6,858,395 B2
DATED : February 22, 2005
INVENTOR(S) : Kaufman

It is certified that error appears in the above-identified patent and that said Letters Patent is hereby corrected as shown below:

<u>Column 33,</u>
Lines 1 and 2, in step (d), delete "transcription or" before "translation".
Lines 4-5, delete "normal individual." and replace with -- normal individual; --.
Line 6, insert -- (e) detecting a translation product of a laminin gene using a detectable laminin-specific antibody, whereby scapuloperoneal muscular dystrophy is diagnosed when laminin expression is normal and α7A integrin expression is reduced in the muscle tissue sample. --.

Signed and Sealed this

Sixteenth Day of May, 2006

JON W. DUDAS
*Director of the United States Patent and Trademark Office*